(12) United States Patent
Akireddy et al.

(10) Patent No.: US 8,809,397 B2
(45) Date of Patent: Aug. 19, 2014

(54) NICOTINIC RECEPTOR NON-COMPETITIVE ANTAGONISTS

(75) Inventors: Srinivasa Rao Akireddy, Winson-Salem, NC (US); Balwinder Singh Bhatti, Winston-Salem, NC (US); Ronald Joseph Heemstra, Lewisville, NC (US); Matt S. Melvin, Winston-Salem, NC (US); Jason D. Speake, Winston-Salem, NC (US); Yunde Xiao, Clemmons, NC (US); Daniel Yohannes, Winston-Salem, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 13/699,757

(22) PCT Filed: May 24, 2011

(86) PCT No.: PCT/US2011/037630
§ 371 (c)(1),
(2), (4) Date: Mar. 22, 2013

(87) PCT Pub. No.: WO2011/149859
PCT Pub. Date: Dec. 1, 2011

(65) Prior Publication Data
US 2013/0203860 A1     Aug. 8, 2013

Related U.S. Application Data

(60) Provisional application No. 61/375,606, filed on Aug. 20, 2010, provisional application No. 61/349,027, filed on May 27, 2010.

(51) Int. Cl.
*A61K 31/13*     (2006.01)
*C07C 45/00*     (2006.01)

(52) U.S. Cl.
USPC .......................................... 514/661; 564/460

(58) Field of Classification Search
USPC .......................................... 514/661; 564/460
See application file for complete search history.

(56) References Cited

U.S. PATENT DOCUMENTS

| | | | |
|---|---|---|---|
| 5,583,140 A | 12/1996 | Bencherif et al. | |
| 5,597,919 A | 1/1997 | Dull et al. | |
| 5,852,041 A | 12/1998 | Cosford et al. | |
| 5,853,696 A | 12/1998 | Elmaleh et al. | |
| 5,969,144 A | 10/1999 | London et al. | |
| 6,310,043 B1 | 10/2001 | Bundle et al. | |
| 7,799,782 B2 * | 9/2010 | Munson et al. | 514/234.5 |
| 2001/0056084 A1 | 12/2001 | Allgeier et al. | |

FOREIGN PATENT DOCUMENTS

| | | |
|---|---|---|
| WO | WO94/08992 | 4/1994 |
| WO | WO96/31475 | 10/1996 |
| WO | WO96/40682 | 12/1996 |
| WO | WO98/25619 | 6/1998 |
| WO | WO03/080046 | 10/2003 |
| WO | WO03/087102 | 10/2003 |

OTHER PUBLICATIONS

Arias, H. R Bhumireddy, R, Anesthetics as chemical tools to study the structure and function of nicotinic acetylcholine receptors, Current Protein & Peptide Science 6: 451-472 (2005).
Arias, H. R. & Blanton; M. P., Molecular and physicochemical aspects of local anesthetics acting on nicotinic acetylcholine receptor-containing membranes, Mini Reviews in Medicinal Chemistry 2: 385-410 (2002).
Arias, H. R., Binding sites for exogenous and endogenous non-competitive inhibitors of the nicotinic acetylcholine receptor, Biochimica et Biophysical Acta—Reviews on Biomembranes 1376: 173-220 (1998).
Arias, H. R., Role of local anesthetics on both cholinergic and serotonergic ionotropic receptors, Neuroscience and Biobehavioral Reviews 23: 817-843 (1999).
Arias, H.R., Bhumireddy, P., Bouzat, C., Molecular mechanisms and binding site locations for noncompetitive antagonists of nicotinic acetylcholine receptors. The International Journal of Biochemistry & Cell Biology 36: 1254-1276 6 (2006).
Arneric, et al., Neuronal nicotinic receptors: A perspective on two decades of drug discovery research, Biochemical Pharmacology, 74: 1092-1101 (2007).
Arneric, S., et al., "Cholinergic channel modulators as a novel therapeutic strategy for Alzheimer's disease," Exp. Opin. Invest. Drugs, 5(1): 79-100 (1996).
Arneric, S., et al., "Preclinical Pharmacology of ABT-418: A Prototypical Cholinergic Channel Activator for the Potential Treatment of Alzheimer's Disease," CNS Drug Rev., 1(1): 1-26 (1995).
Bannon, et al., "Broad-Spectrum, Non-Opioid Analgesic Activity by Selective Modulation of Neuronal Nicotinic Acetylcholine Receptors," *Science* 279: 77-80 (1998).
Bencherif, M., et al., "RJR-2403: A Nicotinic Agonist with CNS Selectivity I: In Vitro Characterization," J. Pharmacol. Exper. Therapeutics, 279(3): 1413-1421 (1996).
Chiari, A., et al., "Sex Differences in Cholinergic Analgesia I: A Supplemental Nicotinic Mechanism in Normal Females," *Anesthesiology*, 91(5): 1447-1454 (1999).
Damaj, M.I., et al., "Antinociceptive and Pharmacological Effects of Metanicotine, a Selective Nicotinic Agonist," *J. Pharmacol. Exp. Ther.*, 291(1): 390-398 (1999).
Gream et al., Aust. J. Chem. 27: 543-65 (1974).
Green et al., *Protecting Groups in Organic Synthesis*, 3rd Edition, John Wiley & Sons 1999.
Heeschen, C. et at, "A novel angiogenic pathway mediated by non-neuronal nicotinic acetylcholine receptors," *J. Clin. Invest.* 110(4):527-36 (2002).

(Continued)

Primary Examiner — Rei-tsang Shiao
(74) Attorney, Agent, or Firm — Womble Carlyle Sandridge & Rice, LLP; Amy H. Fix

(57) ABSTRACT

The present invention relates to compounds that modulate nicotinic receptors as non-competitive antagonists, methods for their synthesis, methods for use, and their pharmaceutical compositions.

10 Claims, No Drawings

(56) References Cited

OTHER PUBLICATIONS

Holladay, M. W., et al., "Neuronal Nicotinic Acetylcholine Receptors as Targets for Drug Discovery," J. Med. Chem., 40(26): 4169-4194 (1997).

Lavand'homme, P., and J.C. Eisenach, "Sex Differences in Cholinergic Analgesia II: Differing Mechanisms in Two Models of Allodynia," Anesthesiology, 91(5): 1455-1461 (1999).

Lippiello et al., "RJR-2403 A Nicotinic Agonist with CNS Selectivity II. In Vivo Characterization," The Journal of Pharmacology and Experimental Therapeutics, vol. 279, No. 3, pp. 1422-1429, 1996.

Tracey et al., "The Inflammatory Reflex," Nature, vol. 420, 2002, pp. 853-859.

Williams, M., et al., "Neuronal Nicotinic Acetylcholine Receptors," DN&P, 7(4): 205-223 (1994).

Connolly, J., Boulter, J., & Heinemann, S. F., Alpha 4-beta 2 and other nicotinic acetylcholine receptor subtypes as targets of psychoactive and addictive drugs, British Journal of Pharmacology 105: 657-686 (1992).

Krasowski, M. D., & Harrison, N. L., General anaesthetic actions on ligand-gated ion channels, Cellular and Molecular Life Sciences. 55 1278-1303 (1999).

Flood, P. & Krasowski M. D., Intravenous anesthetics differentially modulate ligand-gated ion channels, Anesthesiology 92: 1418-1425 (2000).

Ho, K. K. & Flood, P., Single amino acid residue in the extracellular portion of transmembrane segment 2 in the nicotinic a7 acetylcholine receptor modulates sensitivity to ketamine, Anesthesiology 100: 657-662 (2004).

Buisson, B., & Bertrand, D., Open-channel blockers at the human a4β2 neuronal nicotinic acetylcholine receptor, Molecular Pharmacology 53: 555-563 (1998).

Black and Vogel, Helv, Chim. Acta 67: 1612 (1984).

Kozikowski and Schmiesing, J. Org, Chem. 48: 1000-1007 (1983).

Garcia-Colunga, Vazquez-Gomez, E., & Miledi, R., Combined actions of zinc and fluoxetine on nicotinic acetylcholine, receptors, The Pharmacogenornics Journal 4: 388-393 (2004).

Giniatullin, R.A., Sokolova, E.M, Di Angelantonio, S., Skorinkin, A,, Telantova, M.V., Nistri, A, Rapid Relief of Block by Mecamylamine of Neuronal Nicotinic Acetylcholine Receptors of Rat Chromaffin Cells in Vitro: An Electrophysiological and Modeling Study. Molecular Pharmacology 58 778-787 (2000).

Garcia-Colunga, w., Awad: J.N., & Miledi, R., Blockage of muscle and neuronal nicotinic acetylcholine receptors by fluoxetine (Prozac), Proceedings of the National Academy of Sciences USA 94: 2041-2044 (1997).

Gurnilar, F., Arias, H.R., Spitzmaul, G, Bouzat, C., Molecular mechanisms of inhibition of nicotinic. Acetylcholine receptors by tricyclic antidepressants. Neuropharmacology 45: 964-76 (2003).

\* cited by examiner

NICOTINIC RECEPTOR NON-COMPETITIVE ANTAGONISTS

CROSS REFERENCE TO RELATED APPLICATION

This application claims priority to PCT Application Number PCT/US2011/037630, with an International Filing Date of May 24, 2011, which claims priority to U.S. Provisional Patent Application Ser. No. 61/349,027, filed May 27, 2010 and U.S. Provisional Patent Application Ser. No. 61/1375,606 filed Aug. 20, 2010, each of which is herein incorporated by reference in its entirety.

FIELD OF THE INVENTION

The present invention relates to compounds that modulate nicotinic receptors as non-competitive modulators (e.g., non-competitive antagonists), methods for their synthesis, methods for use, and their pharmaceutical compositions.

BACKGROUND OF THE INVENTION

Nicotinic receptors are targets for a great number of exogenous and endogenous compounds that allosterically modulate their function. See, Arias, H. R., Binding sites for exogenous and endogenous non-competitive inhibitors of the nicotinic acetylcholine receptor, *Biochimica et Biophysica Acta—Reviews on Biomembranes* 1376: 173-220 (1998) and Arias, H. R., Bhumireddy, P., Anesthetics as chemical tools to study the structure and function of nicotinic acetylcholiine receptors, *Current Protein & Peptide Science* 6: 451-472 (2005). The function of nicotinic receptors can be decreased or blocked by structurally different compounds called non-competitive modulators, including non-competitive antagonists (reviewed by Arias, H. R. Bhumireddy, P., Bouzat, C., Molecular mechanisms and binding site locations for non-competitive antagonists of nicotinic acetylcholine receptors. *The International Journal of Biochemistry & Cell Biology* 38: 1254-1276 (2006)).

Non-competitive modulators comprise a wide range of structurally different compounds that inhibit receptor function by acting at a site or sites different from the orthosteric binding site. Receptor modulation has proved to be highly complex. The mechanisms of action and binding affinities of non-competitive modulators differ among nicotinic receptor subtypes (Arias et al., 2006). Non-competitive modulators may act by at least two different mechanisms: an allosteric and/or a steric mechanism.

An allosteric antagonist mechanism involves the binding of a non-competitive antagonist to the receptor and stabilization of a non-conducting conformational state, namely, a resting or desensitized state, and/or an increase in the receptor desensitization rate.

In contrast, a straightforward representation of a steric mechanism is that an antagonist molecule physically blocks the ion channel. Such antagonists may be termed non-competitive channel modulators (NCMs). Some inhibit the receptors by binding within the pore when the receptor is in the open state; thereby physically blocking ion permeation. While some act only as pure open-channel blockers, others block both open and dosed channels. Such antagonists inhibit ion flux through a mechanism that does not involve binding at the orthosteric sites.

Barbiturates, dissociative anesthetics, antidepressants, and certain steroids have been shown to inhibit nicotinic receptors by allosteric mechanisms, including open and closed channel blockade. Studies of barbiturates support a model whereby binding occurs to both open and dosed states of the receptors, resulting in blockade of the flow of ions. See; Dilger, J. P., Boguslaysky, R., Barann, M., Katz, T., Vidal, A. M., Mechanisms of barbiturate inhibition of acetylcholine receptor channels, *Journal General Physiology* 109: 401-414 (1997). Although the inhibitory action of local anesthetics on nerve conduction is primarily mediated by blocking voltage gated sodium channels, nicotinic receptors are also targets of local anesthetics. See, Arias, H. R., Role of local anesthetics on both cholinergic and serotonergic ionotropic receptors, *Neuroscience and Biobehavioral Reviews* 23: 817-843 (1999) and Arias, H. R. & Blanton; M. P., Molecular and physicochemical aspects of local anesthetics acting on nicotinic acetylcholine receptor-containing membranes, *Mini Reviews in Medicinal Chemistry* 2; 385-410 (2002).

For example, tetracaine binds to the receptor channels preferentially in the resting state. Dissociative anesthetics inhibit several neuronal-type nicotinic receptors in clinical concentration ranges, with examples such as phencyclidine (PCP) (Connolly, J., Boulter, J., & Heinemann, S. F., Alpha 4-beta 2 and other nicotinic acetylcholine receptor subtypes as targets of psychoactive and addictive drugs, *British Journal of Pharmacology* 105: 657-666 (1992)), ketamine (Flood, P. & Krasowski M. D., Intravenous anesthetics differentially modulate ligand-gated ion channels, *Anesthesiology* 92: 1418-1425 (2000), and Ho, K. K. & Flood, P., Single amino acid residue in the extracellular portion of transmembrane segment 2 in the nicotinic α7 acetylcholine receptor modulates sensitivity to ketamine, *Anesthesiology* 100: 657-662 (2004)), and dizocilpine (Krasowski, M. D., & Harrison, N. General anaesthetic actions on ligand-gated on channels, *Cellular and Molecular Life Sciences* 55: 1278-1303 (1999)). Studies indicate that the dissociative anesthetics bind to a single or overlapping sites in the resting ion channel, and suggest that the ketamine/PCP locus partially overlaps the tetracaine binding site in the receptor channel. Dizocilpine, also known as MK-801, is a dissociative anesthetic and anti-convulsant which also acts as a non-competitive antagonist at different nicotinic receptors. Dizocilpine is reported to be an open-channel blocker of α4β2 neuronal nicotinic receptors. See, Buisson, B., & Bertrand, D., Open-channel blockers at the human α4β2 neuronal nicotinic acetylcholine receptor, *Molecular Pharmacology* 53: 555-563 (1998).

In addition to their well-known actions on monoamine and serotonin reuptake systems, antidepressants have also been shown to modulate nicotinic receptors. Early studies showed that tricyclic antidepressants act as non-competitive antagonists. See; Gumilar, F., Arias, H. R., Spitzmaul, G., Bouzat, C., Molecular mechanisms of inhibition of nicotinic acetylcholine receptors by tricyclic antidepressants. *Neuropharmacology* 45: 964-76 (2003). Garćia-Colunga et al., report that fluoxetine, a selective serotonin reuptake inhibitor (SSRI), inhibits membrane currents elicited by activation of muscle or neuronal nicotinic receptors in a non-competitive manner; either by increasing the rate of desensitization and/or by inducing channel blockade. See, Garćia-Colunga, w., Awad; J. N., & Miledi, R., Blockage of muscle and neuronal nicotinic acetylcholine receptors by fluoxetine (Prozac). *Proceedings of the National Academy of Sciences USA* 94: 2041-2044 (1997); and Garćia-Colunge, J., Vazquez-Gomez, E., & Miledi, R., Combined actions of zinc and fluoxetine on nicotinic acetylcholine, receptors, *The Pharmacogenomics Journal* 4: 388-393 (2004). Mecamylamine, previously approved for the treatment of hypertension, is a classical non-competitive nicotinic receptor antagonist, and is also well known to inhibit receptor function by blocking the ion channel. See, Giniatullin, R. A., Sokolova, E. M. Di Angelantonio, S., Skorinkin, A., Talantova, M. V., Nistri, A, Rapid Relief of Block by Mecamylamine of Neuronal Nicotinic Acetylcholine Receptors of Rat Chromaffin Cells In Vitro: An Electrophysiological and Modeling Study. *Molecular Pharmacology* 58: 778-787 (2000).

SUMMARY OF THE INVENTION

The present invention includes compounds of Formula I:

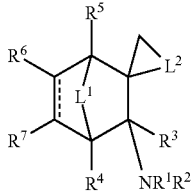

Formula I wherein each of $R^1$ and $R^2$ individually is H, $C_{1-6}$ alkyl, or aryl-substituted $C_{1-6}$ alkyl, or $R^1$ and $R^2$ combine with the nitrogen atom to which they are attached to form a 3- to 8-membered ring, which ring may be optionally substituted with $C_{1-6}$ alkyl, aryl, $C_{1-6}$ alkoxy, or aryloxy substituents;

$R^3$ is H, $C_{1-6}$ alkyl, or $C_{1-6}$ alkoxy-substituted $C_{1-6}$ alkyl;

each of $R^4$, $R^5$, $R^6$, and $R^7$ individually is H, $C_{1-6}$ alkyl, or $C_{1-6}$ alkoxy;

$L^1$ is a linker species selected from the group consisting of $CR^8R^9$, $CR^8R^9CR^{10}R^{11}$, and O;

$L^2$ is a linker species selected from the group consisting of $CH_2$, $CH_2CH_2$, $CH_2CH_2CH_2$, or $CH_2CH_2CH_2CH_2$;

each of $R^8$, $R^9$, $R^{10}$, and $R^{11}$ individually is hydrogen or $C_{1-6}$ alkyl; and the dashed line indicates en optional double bond;

or a pharmaceutically acceptable salt thereof.

The present invention includes pharmaceutical compositions comprising a compound of the present invention or a pharmaceutically acceptable salt thereof. The pharmaceutical compositions of the present invention can be used for treating or preventing a wide variety of conditions or disorders, and particularly those disorders characterized by dysfunction of nicotinic cholinergic neurotransmission or the degeneration of the nicotinic cholinergic neurons.

The present invention includes a method for treating or preventing disorders and dysfunctions, such as CNS disorders and dysfunctions, and also for treating or preventing certain conditions, for example, alleviating pain, hypertension, and inflammation, in mammals in need of such treatment. The methods involve administering to a subject a therapeutically effective amount of a compound of the present invention, including a salt thereof, or a pharmaceutical composition that includes such compounds.

DETAILED DESCRIPTION OF THE INVENTION

I. Compounds

One embodiment of the present invention includes compounds of Formula I:

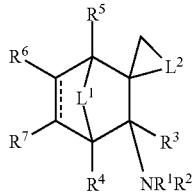

Formula I wherein each of $R^1$ and $R^2$ individually is H, $C_{1-6}$ alkyl, or aryl-substituted $C_{1-6}$ alkyl, or $R^1$ and $R^2$ combine with the nitrogen atom to which they are attached to form a 3- to 8-membered ring, which ring may be optionally substituted with $C_{1-6}$ alkyl, aryl, $C_{1-6}$ alkoxy, or arylon, substituents;

$R^3$ is H, $C_{1-6}$ alkyl, or $C_{1-6}$ alkoxy-substituted $C_{1-6}$ alkyl;

each of $R^4$, $R^5$, $R^6$ and $R^7$ individually is H, $C_{1-6}$ alkyl, or $C_{1-6}$ alkoxy;

$L^1$ is a linker species selected from the group consisting of $CR^8R^9$, $CR^8R^9CR^{10}R^{11}$, and O;

$L^2$ is a linker species selected from the group consisting of $CH_2$, $CH_2CH_2$, $CH_2CH_2CH_2$, or $CH_2CH_2CH_2CH_2$;

each of $R^8$, $R^9$, $R^{10}$, and $R^{11}$ individually is hydrogen or $C_{1-6}$ alkyl; and the dashed line indicates an optional double bond:

or a pharmaceutically acceptable salt thereof.

In one embodiment, $R^1$ is H and $R^2$ is $C_{1-6}$ alkyl. In one embodiment, $R^3$ is $C_{1-6}$ alkyl. In one embodiment, each of $R^4$, $R^5$, $R^6$, and $R^7$ is H. In one embodiment $L^1$ is $CR^8R^9$, and each of $R^8$ and $R^9$ is hydrogen. In one embodiment, $L^2$ is $CH_2CH_2$. In one embodiment, the dashed line is a single bond.

One aspect of the present invention includes a pharmaceutical composition comprising a compound of the present invention and a pharmaceutically acceptable carrier.

One aspect of the present invention includes a method for the treatment or prevention of a disease of condition mediated by a neuronal nicotinic receptor, specifically through the use of non-competitive modulators (e.g., non-competitive antagonists), including but not limited channel blockers, comprising the administration of a compound of the present invention. In one embodiment, the disease or condition is a CNS disorder. In another embodiment, the disease or condition is Inflammation or an inflammatory response. In another embodiment, the disease or condition is pain. In another embodiment, the disease or condition is neovascularization. In another embodiment, the disease or condition is hypertension. In another embodiment, the disease or condition is another disorder described herein.

One aspect of the present invention includes use of a compound of the present invention for the preparation of a medicament for the treatment or prevention of a disease or condition mediated by a neuronal nicotinic, receptor, specifically through the use of non-competitive antagonists, such as channel blockers. In one embodiment, the disease or condition is a CNS disorder. In another embodiment, the disease or condition is inflammation or an inflammatory response. In another embodiment, the disease or condition is pain. In another embodiment, the disease or condition is neovascularization. In another embodiment, the disease or condition is hypertension. In another embodiment, the disease or condition is another disorder described herein.

One aspect of the present invention includes a compound of the present invention for use as an active therapeutic substance. One aspect, thus, includes a compound of the present invention for use in the treatment or prevention of a disease or condition mediated by a neuronal nicotinic receptor, specifically through the use of non-competitive antagonists, such as channel blockers. In one embodiment, the disease or condition is a CNS disorder. In another embodiment, the disease or condition is inflammation or an inflammatory response. In another embodiment, the disease or condition is pain. In another embodiment, the disease or condition is neovascularization. In another embodiment, the disease or condition is hypertension. In another embodiment, the disease or condition is another disorder described herein.

Particular diseases or conditions include depression, including major depressive disorder, hypertension, irritable bowel syndrome (IBS), including IBS-D (diarrhea predominant), over active bladder (OAB), and addiction, including smoking cessation.

The scope of the present invention includes all combinations of aspects and embodiments.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-6}$ alkyl represents a straight or branched chain hydrocarbon containing one to six carbon atoms.

As used herein the term "alkyl" refers to a straight or branched chain hydrocarbon, which may be optionally substituted, with multiple degrees of substitution being allowed. Examples of "alkyl" as used herein include, but are not limited to methyl, ethyl, propyl, isopropyl, isobutyl, n-butyl, tert-butyl, isopentyl, and n-pentyl.

As used herein, the term "alkylene" refers to a divalent group, such as "methylene," "ethylene," and "ethenylene," which refer to divalent forms —$CH_2$—, —$CH_2$—$CH_2$—, and —CH=CH— respectively.

As used herein, the term "aryl" refers to a single benzene ring or fused benzene ring system which may be optionally substituted, with multiple degrees of substitution being allowed. Examples of "aryl" groups as used include, but are not limited to phenyl, 2-naphthyl, 1-naphthyl, anthracene, and phenanthrene. Preferable aryl rings have five- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthylenyl, and also includes such groups as, for non-limiting examples, dihydronaphthalene and tetrahydronaphthalene.

As used herein the term "alkoxy" refers to a group —$OR^a$, where $R^a$ is alkyl as herein defined.

As used herein the term "aryloxy" refers to a group —$OR^a$, where $R^a$ is aryl as herein defined.

As used herein "amino" refers to a group —$NR^aR^b$, where each of $R^a$ and $R^b$ is hydrogen. Additionally, "substituted amino" refers to a group —$NR^aR^b$ wherein each of $R^a$ and $R^b$ individually is alkyl, arylalkyl or aryl. As used herein, when either $R^a$ or $R^b$ is other than hydrogen, such a group may be referred to as a "substituted amino" or, for example if $R^a$ is H and $R^b$ is alkyl, as an "alkylamino."

As used herein, the term "pharmaceutically acceptable" refers to carrier(s), diluent(s), excipient(s) or salt forms of the compounds of the present invention that are compatible with the other ingredients of the formulation and not deleterious to the recipient of the pharmaceutical composition.

As used herein, the term "pharmaceutical composition" refers to a compound of the present invention optionally admixed with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutic amount" and "effective dose" refer to an amount of the compound of the present invention sufficient to elicit the desired pharmacological or therapeutic effects, thus resulting in an effective treatment of a disorder. Treatment of a disorder may be manifested by delaying or preventing the onset or progression of the disorder, as well as the onset or progression of symptoms associated with the disorder. Treatment of a disorder may also be manifested by a decrease or elimination of symptoms, reversal of the progression of the disorder, as well as any other contribution to the well being of the patient.

The effective dose can vary, depending upon factors such as the condition of the patient, the severity of the symptoms of the disorder, and the manner in which the pharmaceutical composition is administered. Typically, to be administered in an effective dose, compounds may be administered in an amount of less than 5 mg/kg of patient weight. The compounds may be administered in an amount from less than about 1 mg/kg patient weight to less than about 100 µg/kg of patient weight, and further between about 1 µg/kg to less than 100 µg/kg of patient weight. The foregoing effective doses typically represent that amount that may be administered as a single dose, or as one or more doses that may be administered over a 24 hours period.

The compounds of this invention may be made by a variety of methods, including well-established synthetic methods. Illustrative general synthetic methods are set out below and then specific compounds of the invention are prepared in the working Examples.

In the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis, 3rd Edition*, John Wiley & Sons, herein incorporated by reference with regard to protecting groups), These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds useful as intermediates in the preparation of compounds of the present invention along with methods for their preparation.

The compounds can be prepared according to the methods described below using readily available starting materials and reagents. In these reactions, variants may be employed which are themselves known to those of ordinary skill in this art but are not described in detail here.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the invention. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently replacement of hydrogen by deuterium in a biologically active compound may result in a compound that generally retains its biochemical potency and selectivity but manifests significantly different absorption, distribution, metabolism end/or excretion (ADME) properties compared to its isotope-free counterpart. Thus, deuterium substitution may result in improved drug efficacy, safety, and/or tolerability for some biologically active compounds.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

When a compound is desired as a single enantiomer, such may be obtained by stereospecific synthesis, by resolution of the final product or any convenient intermediate, or by chiral chromatographic methods as are known in the art Resolution of the final product, an intermediate, or a starting material may be effected by any suitable method known in the art. See, for example, *Stereochemistry of Organic Compounds* (Wiley-Interscience, 1994).

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galaotarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Those of skill in the art of organic chemistry will appreciate that more than one systematic name can be given to many organic compounds. The scope of the present invention should not be considered as lacking clarity due to the several potential naming conventions possible for the compounds.

II. General Synthetic Methods

Those skilled in the art of organic synthesis will appreciate that there exist multiple means of producing compounds of the present invention, as well as means for producing compounds of the present invention which are labeled with a radioisotope appropriate to various uses.

One means of producing compounds of the present invention is outlined in Scheme 1 (see Synthetic Examples). Thus, norcamphor (2-norbornanone) can be alkylated adjacent to the carbonyl functionality, using techniques well known to those of skill in the art of organic synthesis. Typically, treatment of the ketone with strong base (e.g., sodium hydride, sodium alkoxide, sodium amide) to form an enolate intermediate, followed by treatment with an alkyl halide or sulfonate, is used for such transformations. Under certain conditions, the alkylation can be performed with an α,ω-dihaloalkane (such as 1,3-dibromopropane), such that a spiro linkage is formed. While Scheme 1 shows the formation of a spirocyclobutane (Compound II), other ring sizes (e.g., spirocyclopentane) are also accessible in this manner, by using other α,ω-dihaloalkanes. The carbonyl functionality can subsequently be converted into an exocyclic methylene (Compound III), using Wittig (or equivalent) chemistry. Treatment of exo-methylene compounds with hydrogen cyanide (or similar reagents, such as thiocyanates), in the presence of strong acid, can provide the corresponding tertiary formamido compounds, in a process known as the Ritter reaction. Reduction of the formamido compound, using a hydride reducing agent, such as lithium aluminum hydride or sodium bis(methoxyethoxy)aluminum hydride, gives the corresponding secondary amine, Compound IV.

Alternatively, substituted 2-norbornanones can also be used as starting materials in the transformation outlined in Scheme 2. Thus, each of D-camphor and L-camphor (both commercially available) can be transformed into stereoisomers of Compound V. Other ketone starting materials can also be used. For instance, the homolog of 2-norbornanone, bicyclo[2,2,2]octan-2-one, can be made by hydrogenation of bicyclo[2,2,2]oct-5-en-2-one, which in turn can be made by procedures similar to those published by Kozikowski and Schmiesing, J. Org. Chem. 48: 1000-1007 (1983), herein incorporated by reference with regard to such reaction. Similarly, 7-oxabicyclo[2.2.1]hept-5-en-2-one, produced as described by Black and Vogel, Helv. Chim. Acta 67: 1612 (1984), herein incorporated by reference with regard to such reaction, can be hydrogenated to give 7-oxabicyclo[2.2.1]

heptan-2-one. Each of these ketones is a potential starting material for transformations similar to those shown in Schemes 1 and 2.

The spirocyclopropane functionality can be installed using Simmons-Smith and similar chemistries. Thus, reaction of 3-methylene-2-norbornanone with diiodomethane in the presence of zinc-copper couple gives spiro[bicyclo[2.2.1] heptane-2,1'-cyclopropan]-3-one, which can then be transformed into compounds of the resent invention utilizing reactions, already described. Certain spirocyclopropane-containing compounds are known in the literature and also serve as a starting point for synthesis of compounds of the present invention. See, for instance, Dream and Pincombe, Aust. J. Chem. 27: 543-565 (1974), herein incorporated by reference with regard to such reaction.

Secondary amines, such as Compounds IV and V, can be converted into tertiary amines through the intermediacy of amides and carbamates. Thus, sequential treatment of such compounds with di-tert-butyl dicarbonate and lithium aluminum hydride will produce the corresponding N-methyl tertiary mine.

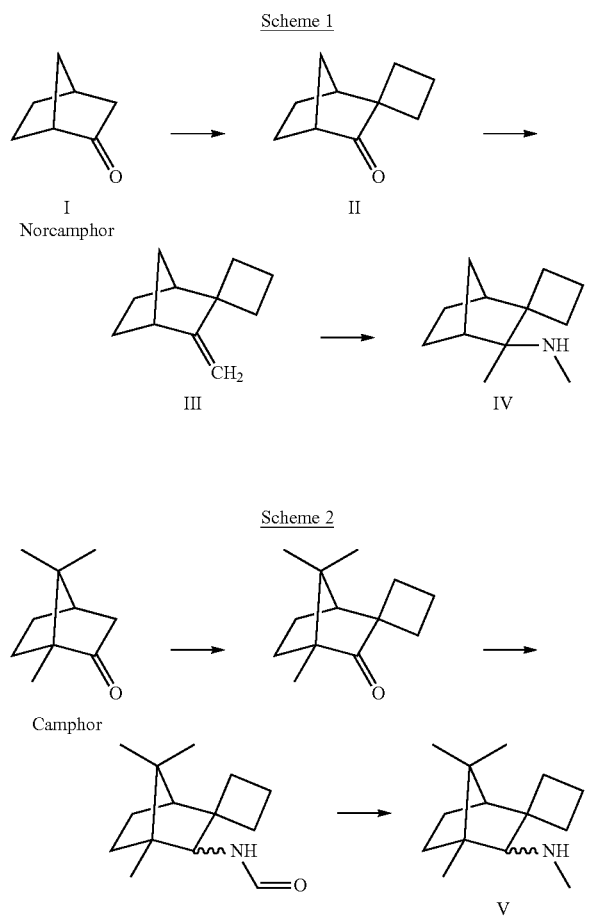

The incorporation of specific radioisotopes is also possible. For example, reductions of amides and carbamates with lithium aluminum deuteride or lithium aluminum tritide reducing agents can produce N-trideuteromethyl or N-tritriliomethyl amines. Alternatively, generation of an amide or carbamate, in which the carbonyl carbon is an $^{11}C$, $^{13}C$, or $^{14}C$ atom, followed by reduction with lithium aluminum hydride, will produce an amine with the $^{11}C$, $^{13}C$, or $^{14}C$ atom, respectively, incorporated. The incorporation of specific radioisotopes is often desirable in the preparation of compounds that are to be used in a diagnostic setting (e.g., as imaging agents) or in functional and metabolic studies, III. Pharmaceutical Compositions Although it is possible to administer the compound of the present invention in the form of a bulk active chemical, it is preferred to administer the compound in the form of a pharmaceutical composition or formulation. Thus, one aspect the present invention includes pharmaceutical compositions comprising one or more compounds of Formula I and/or pharmaceutically acceptable salts thereof and one or more pharmaceutically acceptable carriers, diluents, or excipients. Another aspect of the invention provides a process for the preparation of a pharmaceutical composition including admixing one or more compounds of Formula I and/or pharmaceutically acceptable salts thereof with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions. The pharmaceutical compositions of the present invention may be provided in modified release dosage forms such as time-release tablet and capsule formulations.

The pharmaceutical compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses The administration of the pharmaceutical compositions described herein can be intermittent, or at a gradual, continuous, constant or controlled rate. The pharmaceutical compositions may be administered to a warm-blooded animal, for example, a mammal such as a mouse, rat, cat, rabbit, dog, pig, cow, or monkey; but advantageously is administered to a human being. In addition, the time of day and the number of times per day that the pharmaceutical composition is administered can vary.

The compounds of the present invention may be used in the treatment of a variety of disorders and conditions and, as such, may be used in combination with a variety of other suitable therapeutic agents useful in the treatment or prophylaxis of those disorders or conditions. Thus, one embodiment of the present invention includes the administration of the compound of the present invention in combination with other therapeutic compounds. For example, the compound of the present invention can be used in combination with other NNR ligands (such as varenicline), allosteric modulators of NNRs, antioxidants (such as free radical scavenging agents), antibacterial agents (such as penicillin antibiotics), antiviral agents (such as nucleoside analogs, like zidovudine and acyclovir), anticoagulants such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, antidepressants (such as imipramine, fluoxetine, paroxetine, escitalopram, sertraline, venlafaxine, and duloxetine), anxiolytics (such as alprazolam and buspirone), anticonvulsants such as phenyloin and gabapentin), vasodilators (such as prazosin and sildenafil), mood stabilizers (such as valproate and aripiprazole), anti-cancer drugs (such as anti-proliferatives), anti-hypertensive agents (such as atenolol, donidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole). Such a combination of pharmaceutically active agents may be administered together or separately and when administered separately, administration may occur simultaneously or sequentially, in any order. The amounts of the compounds or agents and the relative timings of administration will be selected in order to achieve the desired therapeutic effect. The administration in combination of a compound of the present invention with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second. Such sequential administration may be close in time or remote in time.

Another aspect of the present invention includes combination therapy comprising administering to the subject a therapeutically or prophylactically effective amount of the compound of the present invention and one or more other therapy including chemotherapy, radiation therapy, gene therapy, or immunotherapy.

IV. Method of Using Pharmaceutical Compositions

The compounds of the present invention can be used for the prevention or treatment of various conditions or disorders for which other types of nicotinic compounds have been proposed or are shown to be useful as therapeutics, such as CNS disorders, inflammation, inflammatory response associated with bacterial and/or viral infection, pain, metabolic syndrome, autoimmune disorders, addictions, obesity or other disorders described in further detail herein. This compound can also be used as a diagnostic agent (in vitro and in vivo). Such therapeutic and other teachings are described, for example, in references previously listed herein, including Williams et al., *Drug News Perspec.* 7(4): 205 (1994), Arneric et al., *CNS Drug Rev.* 1(1): 1-26 (1995), Arneric et al., *Exp. Opin. Invest. Drugs* 5(1); 79-100 (1996), Bencherif et al., *J. Pharmacol. Exp. Ther.* 279: 1413 (1996), Lippiello et al., *J. Pharmacol. Exp. Ther.* 279: 1422 (1996), Damaj et el., *J. Pharmacol, Exp. Ther.* 291: 390 (1999); Chiari et al., *Anesthesiology* 91: 1447 (1999), Lavand'homme and Eisenbach, *Anesthesiology* 91: 1455 (1999), Holladay et al., *J. Med. Chem.* 40(28): 4169-94 (1997), Bannon et el., *Science* 279: 77 (1998), PCT WO 94/08992, PCT WO 96/31475, PCT WO 96/40582, and U.S. Pat. No. 5,583,140 to Beripherif et al., U.S. Pat. No. 5,597,919 to Dull et al., U.S. Pat. No. 5,604,231 to Smith et al, and U.S. Pat. No. 5,852,041 to Cosford et al.

CNS Disorders

The compounds and their pharmaceutical compositions are useful in the treatment or prevention of a variety of CNS disorders, including neurodegenerative disorders, neuropsychiatric disorders, neurologic disorders, and addictions. The compounds and their pharmaceutical compositions can be used to treat or prevent cognitive deficits and dysfunctions, age-related and otherwise; attentional disorders and dementias, including those due to infectious agents or metabolic disturbances; to provide neuroprotection; to treat convulsions and multiple cerebral infarcts; to treat mood disorders, compulsions and addictive behaviors; to provide analgesia; to control inflammation, such as mediated by cytokines and nuclear factor kappa B; to treat inflammatory disorders; to provide pain relief; and to treat infections, as anti-infectious agents for treating bacterial, fungal, and viral infections. Among the disorders, diseases and conditions that the compounds and pharmaceutical compositions of the present invention can be used to treat or prevent are age-associated memory impairment (AAMI), mild cognitive impairment (MCI), age-related cognitive de-cline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, vascular dementia. Down syndrome, head trauma, traumatic brain injury (TBI), dementia pugilistica, Creutzfeld-Jacob Disease and prion diseases, stroke, central ischemia, peripheral ischema, attention deficit disorder, attention deficit hyperactivity disorder, dyslexia, schizophrenia, schizophreniform disorder, schizoaffective disorder, cognitive dysfunction if schizophrenia, cognitive deficits in schizophrenia, Parkinsonism including Parkinson's disease, postencephalitic parkinsonism, parkinsonism-dementia of Gaum, frontotemporal dementia Parkinson's Type (FTDP), Pick's disease, Niemann-Pick's Disease, Huntington's Disease, Huntington's chorea, dyskinesia, tardive dyskinesia, spastic dystonia, hyperkinesia, progressive supranuclear palsy, progressive supranuclear paresis, restless leg syndrome, Creutzfeld-Jakob disease, multiple sclerosis, amyotrophic lateral sclerosis (ALS), motor neuron diseases (MND), multiple system atrophy (MSA), corticobasal degeneration, Guillain-Barré Syndrome (GBS), and chronic inflammatory demyelinating polyneuropathy (CIDP), epilepsy, autosomal dominant nocturnal frontal lobe epilepsy, mania, anxiety, depression, including major depressive disorder (MDD), premenstrual dysphoria, panic disorders, bulimia, anorexia, narcolepsy, excessive daytime sleepiness, bipolar disorders, generalized anxiety disorder, obsessive compulsive disorder, rage outbursts, conduct disorder, oppositional defiant disorder, Tourette's syndrome, autism, drug and alcohol addiction, tobacco addiction and thus, useful as an agent for smoking cessation, compulsive overeating and sexual dysfunction.

Cognitive impairments or dysfunctions may be associated with psychiatric disorders or conditions, such as schizophrenia and other psychotic disorders, including but not limited to psychotic disorder, schizophreniform disorder, schizoaffective disorder, delusional disorder, brief psychotic disorder, shared psychotic disorder, and psychotic disorders due to a general medical conditions, dementias and other cognitive disorders, including but not limited to mild cognitive impairment pre-senile dementia, Alzheimer's disease, senile dementia, dementia of the Alzheimer's type, age-related memory impairment, Lewy body dementia, vascular dementia, AIDS dementia complex, dyslexia. Parkinsonism including Parkinson's disease, cognitive impairment and dementia of Parkinson's Disease, cognitive impairment of multiple sclerosis, cognitive impairment caused by traumatic brain injury, dementias due to other general medical conditions, anxiety disorders, including but not limited to panic disorder without agoraphobia, panic disorder with agoraphobia, agoraphobia without history of panic disorder, specific phobia, social phobia, obsessive-compulsive disorder, post traumatic stress disorder, acute stress disorder, generalized anxiety disorder and generalized anxiety disorder due to a general medical condition, mood disorders, including but not limited to major depressive disorder, dysthymic disorder, bipolar depression, bipolar mania, bipolar I disorder, depression associated with manic, depressive or mixed episodes; bipolar II disorder, cyclothymic disorder, and mood disorders due to general medical conditions, sleep disorders, including but not limited to dyssomnia disorders, primary insomnia, primary hypersomnia, narcolepsy, parasomnia disorders, nightmare disorder, sleep terror disorder and sleepwalking disorder, mental retardation, learning disorders, motor skills disorders, communication disorders, pervasive developmental disorders, attention-deficit and disruptive behavior disorders, attention deficit disorder, attention deficit hyperactivity disorder, feeding and eating disorders of infancy, childhood, or adults, tic disorders, elimination disorders, substance-related disorders, including but not limited to substance dependence, substance abuse, substance intoxication, substance withdrawal, alcohol-related disorders, amphetamine or amphetamine-like-related disorders, caffeine-related disorders, cannabis-related disorders, cocaine-related disorders, hallucinogen-related disorders, inhalant-related disorders, nicotine-related disorders, opioid-related disorders, phencyclidine or phencyclidine-like-related disorders, and sedative-, hypnotic- or anxiolytic-related disorders, personality disorders, including but not limited to obsessive-compulsive personality disorder and impulse-control disorders.

Cognitive performance may be assessed with a validated cognitive scale, such as, for example, the cognitive subscale of the Alzheimer's Disease Assessment Scale (ADAS-cog). One measure of the effectiveness of the compounds of the present invention in improving cognition may include measuring a patient's degree of change according to such a scale.

Regarding compulsions and addictive behaviors, the compounds of the present invention may be used as a therapy for nicotine addiction, including as an agent for smoking cessation, and for other brain-reward disorders, such as substance abuse including alcohol addiction, illicit and prescription drug addiction eating disorders, including obesity, and behavioral addictions, such as gambling, or other similar behavioral manifestations of addiction.

The above conditions and disorders are discussed in further detail, for example, in the American Psychiatric Association: Diagnostic and Statistical Manual of Mental Disorders, Fourth Edition, Text Revision, Washington, D.C., American Psychiatric Association, 2000. This Manual may also be referred to for greater detail on the symptoms and diagnostic features associated with substance use, abuse, and dependence.

Inflammation

The nervous system, primarily through the vagus nerve, is known to regulate the magnitude of the innate immune response by inhibiting the release of macrophage tumor necrosis factor (TNF). This physiological mechanism is known as the "cholinergic anti-inflammatory pathway" (see, for example, Tracey, "The inflammatory Reflex," Nature 420: 853-9 (2002)). Excessive inflammation and tumor necrosis factor synthesis cause morbidity and even mortality in a variety of diseases. These diseases include, but are not limited to, endotoxemia, rheumatoid arthritis, osteoarthritis, psoriasis, asthma, atherosclerosis, idiopathic pulmonary fibrosis, and inflammatory bowel disease.

Inflammatory conditions that can be treated or prevented by administering the compounds described herein include, but are not limited to, chronic and acute inflammation, psoriasis, endotoxemia, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, irritable bowel syndrome, including diarrhea predominant IBS, Crohn's disease, ulcers, ulcerative colitis, acute cholangitis, aphthous stomatitis, cachexia, pouchitis, glomerulonephritis, lupus nephritis, thrombosis, and graft vs. host reaction.

Inflammatory Response Associated with Bacterial and/or Viral Infection

Many bacterial and/or viral infections are associated with side effects brought on by the formation of toxins, and the body's natural response to the bacteria or virus and/or the toxins, As discussed above the body's response to infection often involves generating a significant amount of TNF and/or other cytokines. The over-expression of these cytokines can result in significant injury, such as septic shock (when the bacteria is sepsis), endotoxic shock, urosepsis, viral pneumonitis and toxic shock syndrome.

Cytokine expression is mediated by NNRs, and can be inhibited by administering agonists or partial agonists of these receptors. Those compounds described herein that are agonists or partial agonists of these receptors can therefore be used to minimize the inflammatory response associated with bacterial infection, as well as viral and fungal infections. Examples of such bacterial infections include arthrax, botulism, and sepsis. Some of these compounds may also have antimicrobial properties. Furthermore, the compounds can be used in the treatment of Raynaud's disease, namely viral-induced painful peripheral vasoconstriction.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle at al. Other agents effective against bacterial and other toxins can be effective and their therapeutic effect can be complemented by co-administration with the compounds described herein.

Pain

The compounds can be administered to treat and/or prevent pain, including acute, neurologic, inflammatory, neuropathic and chronic pain. The compounds can be used in conjunction with opiates to minimize the likelihood of opiate addiction (e.g., morphine sparing therapy). The analgesic activity of compounds described herein can be demonstrated in models of persistent inflammatory pain and of neuropathic pain, performed as described in U.S. Published Patent Application No 20010056084 A1 (Allgeier et al.) (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiology, in particular in treating inflammatory pain and associated hyperalgesia, neuropathic pain and associated hyperalgesia, chronic pain (e.g., severe chronic pain, postoperative pain and pain associated with various conditions including cancer, angina, renal or biliary colic, menstruation, migraine and gout). Inflammatory pain may be of diverse genesis, including arthritis and rheumatoid disease, tenosynovitis and vasculitis. Neuropathic pain includes trigeminal or herpetic neuralgia, neuropathies such as diabetic neuropathy pain, causalgia, low back pain and deafferentation syndromes such as brachial plexus avulsion.

Neovascularization

Inhibition of neovascularization, for example, by administering antagonists or at certain dosages, partial agonists) of nicotinic receptors can treat or prevent conditions characterized by undesirable neovasculanzation or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of nicotinic receptors.

Specific antagonism of nicotinic receptors reduces the angiogenic response to inflammation, ischemia, and neoplasia. Guidance regarding appropriate animal model systems for evaluating the compounds described herein can be found, for example, in Heeschen, C. et al., "A novel angiogenic pathway mediated by non-neuronal nicotinic acetylcholine receptors," *J. Clin. Invest.* 110(4):527-38 (2002).

Representative tumor types that can be treated using the compounds described herein include SCLC, NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cisplatin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art Other Disorders In addition to treating CNS disorders, inflammation, and neovascularization, and pain, the compounds of the present invention can be also used to prevent or treat certain other conditions, diseases, and disorders in which NNRs play a role. Examples include autoimmune disorders such as lupus, disorders associated with cytokine release, cachexia secondary to infection (e.g., as occurs in AIDS, AIDS related complex and neoplasia), obesity, pemphitis, urinary incontinence, overactive bladder (OAB), diarrhea, constipation, retinal diseases, infectious diseases, myasthenia, Eaton-Lambert syndrome, hypertension, preeclampsia, osteoporosis, vasoconstriction, vasodilatation, cardiac arrhythmias, type I diabetes, type II diabetes, bulimia, anorexia and sexual dysfunction, as well as those indications set forth in published PCT application WO 98/25619. The compounds of this invention can also be administered to treat convulsions such as those that are symptomatic of epilepsy, and to treat conditions such as syphilis and Creutzfeld-Jakob disease.

Compounds of the present invention may be used to treat bacterial infections and dermatologic conditions, such as pemphigus folliaceus, pemphigus vulgaris, and other disorders, such as acantholysis, where autoimmune responses with high ganglionic NNR antibody titer is present. In these disorders, and in other autoimmune diseases, such as Mysthenia Gravis, the fab fragment of the antibody binds to the NNR receptor (crosslinking 2 receptors), which induces internalization and degradation.

Diagnostic Uses

The compounds can be used in diagnostic compositions, such as probes, particularly when they are modified to include appropriate labels. For this purpose the compounds of the present invention most preferably are labeled with the radioactive isotopic moiety $^{11}C$.

The administered compounds can be detected using position emission topography (PET). A high specific activity is desired to visualize the selected receptor subtypes at non-saturating concentrations. The administered doses typically are below the toxic range and provide high contrast images. The compounds are expected to be capable of administration in nontoxic levels Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al., as noted. The compounds can be administered in formulation compositions that incorporate other ingredients, such as those types of ingredients that are useful in formulating a diagnostic composition. Compounds useful in accordance with carrying out the present invention most preferably are employed in forms of high purity. See. U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality. In addition to humans, the compounds can also be administered to animals, such as mice, rats, dogs, and monkeys. SPECT and PET imaging can be carried out using any appropriate technique and apparatus. See Villemagne at al., In: Arneric at al. (Eds.) *Neuronal Nicotinic Receptors: Pharmacology and Therapeutic Opportunities*, 235-250 (1998)

and U.S. Pat. No. 5,853,696 to Elmalch et al., each herein incorporated by reference, for a disclosure of representative imaging techniques.

V. SYNTHETIC EXAMPLES

Example 1

Exo-N,3-dimethylspiro[bicyclo[2.2.1]heptane-2,1'-cyclobutan]-3-amine

To a solution of 2-norbornanone (norcamphor) (16.0 g, 145 mmol) and 1,3-dibromopropane (203 mmol, 20.7 mL; 41.1 g) in diethyl ether (450 mL) was added sodium amide (363 mmol, 14.8 g) and the mixture was stirred at reflux for 24 h. The mixture was poured into 200 mL of ice-water, and the organic layer was separated. The aqueous layer was extracted with 200 mL of ether. The combined ether extracts were concentrated, and the liquid residue was distilled at 60-100° C. at 10-20 Torr vacuum to obtain 14 g of impure product. This was dissolved in 150 mL of hexanes and stirred with a solution of potassium permanganate (12.0 g, 75.9 mind) in water (150 mL) for 5 h. The biphasic mixture was filtered through a bed of diatomaceous earth, which was then washed with hexanes (100 mL). The hexane layer was separated, and the aqueous layer was extracted with 600 mL of hexanes. The hexane layers were combined, concentrated, and purified on silica gel column, eluting with 10-40% ether in hexanes, to obtain spiro[bicyclo[2.2.1]heptane-2,1'-cyclobutan]-3-one (Compound II in Scheme 1) (6.1 g, 28% yield) as oil. $^1$H NMR (CDCl$_3$, 400 MHz): δ 2.55-2.49 (m, 2H). 2.18-2.08 (m, 2H), 2.00-1.58 (m, 7H), 1.49-1.36 (m, 3H); LCMS (m/z): 151 (M+1).

To a suspension of (methyl)triphenylphosphonium bromide (49.9 mmol, 18.2 g) in dry tetrahydrofuran (THF) (100 mL) at −78° C. was added n-butyllithium (46.5 mmol, 18.6 mL of 2.5 M solution in hexanes). The mixture was stirred for 30 min at −78° C. To this mixture was added spiro[bicyclo[2.2.1]heptane-2,1'-cyclobutan]-3-one (5.00 g, 33.3 mmol). The resulting mixture was stirred at ambient temperature for 20 h. Hexanes (300 mL) were added, and the mixture was filtered. The filtrate was concentrated, and the residue was purified on an 80 g silica gel column, eluting with hexanes, to obtain 3-methylenespiro[bicyclo[2.2.1]heptane-2,1'-cyclobutane] (Compound III in Scheme 1) (3.7 g, 75%) as oil. $^1$H NMR (CDCl$_3$, 400 MHz); δ 4.82 (s, 2H), 2.63 (bra, 1H), 2.22 (bra, 1H), 2.05-1.78 (m, 6H), 1.63-1.52 (m. 1H), 1.48-1.34 (m, 3H), 1.21-1.12 (m, 2H).

To a suspension of 3-methylenespiro[bicyclo[2,2,1]heptane-2,1'-cyclobutane](2.10 g, 14.2 mmol) and potassium thiocyanate (14.2 mmol, 1.39 g) was slowly added a solution of sulfuric acid (1.40 g; 14.3 mmol) in water (0.52 mL) over 15 min at 50° C. The solution was stirred at 85° C. for 5.5 h. The solution was cooled to ambient temperature, diluted with toluene (20 mL), and washed sequentially with water (20 mL) and saturated aqueous sodium bicarbonate (10 mL). The toluene layer was collected, dried over anhydrous sodium sulfate, and filtered. To the filtrate was added sodium bis(methoxyethoxy)aluminum hydride (28 mmol, 7.9 mL of 65-70% solution in toluene), and the resulting mixture was stirred at 85° C. for 2 h. The mixture was cooled to 0° C. and a mixture of 3N aqueous sodium hydroxide (3 mL) and 5% sodium hypochlorite (15 mL) was slowly added drop-wise, in intervals. The toluene layer was separated and washed with water (30 mL). The toluene layer was then extracted with 1 N aqueous hydrochloric acid (2×10 mL). The toluene layer was discarded, and the combined hydrochloric acid extracts were made basic by addition of 10% aqueous sodium hydroxide (to pH10). The basic aqueous mixture was extracted with ether (2×30 mL). The ether extracts were collected, concentrated, and purified by silica gel column chromatography, eluting with 0-40% CMA (chloroform:methanol:30% aqueous ammonia, 9:1:0.1) in chloroform, to obtain exo-N,3-dimethylspiro[bicyclo[2.2.1]heptane-2,1'-cyclobutan]-3-amine (0.38 g, 15% yield) (Compound IV in Scheme I) as oil. The oil was dissolved in 5 mL of dichloromethane, cooled in ice-bath, and combined with 2 mL, of 6 M aqueous hydrochloric acid. The mixture was concentrated and vacuum dried to obtain the hydrochloride salt. $^1$H NMR (D$_2$O, 400 MHz): δ 2.41 (s, 3H), 2.24-2.18 (m, 2H), 1.98-1.90 (m, 1H), 1.82-1.74 (m, 1H), 1.67-1.58 (m, 2H), 1.52-1.11 (m, 8H), 0.95 (s, 3H); LCMS (m/z): 180 (M+1).

The exo stereochemistry was established by NMR.

Example 2

Chiral Chromatographic Separation of exo-N,3-dimethylspiro[bicyclo[2.2.1]heptane-2,1'-cyclobutan]-3-amine Exo-N,3-dimethylspiro[bicyclo[2.2.1]heptane-2,1'-cyclobutan]-3-amine (2.0 g) was dissolved in 20 mL of acetonitrile and was separated with 0.2 mL, injections on chiral column (Chiral Pak AD-H, 5 micron, 250×20 cm), using 0.2% diethylamine in acetonitrile/isopropanol (95:5), with a flow rate of 10 mL/min. Fractions containing peak 1 (early eluting) and peak 2 (late eluting) were separately concentrated. The two residues were individually dissolved in 10 mL of dichloromethane, treated with 2 mL of 6N aqueous hydrochloric acid, and concentrated to dryness. These hydrochloride salt products weighed 0.74 g (peak 1) and 0.48 g (peak 2), respectively.

Example 3

N,3-dimethylspiro[bicyclo[2.2.1]heptane-2,1'-cyclopentan]-3-amine

To a solution of 2-norbornanone (25.0 g, 227 mmol) and 1,4-dibromobutane (68.0 g, 317 mmol) in diethyl ether (700 mL) was added sodium amide (23.1 g, 567 mmol). This mixture was heated at reflux for 24 h, cooled and poured into 200 mL of ice-water. The organic layer was collected, and the aqueous layer was extracted with 200 mL, of diethyl ether. The combined diethyl ether extracts were concentrated, and the residue was distilled at 65-80° C. at 7-15 Torr to obtain 19 g of impure product. This was dissolved in hexanes (500 mL) and stirred with aqueous potassium permanganate (30 g, 0.19 mol, in 500 mL) for 5 h. The mixture was filtered, and the hexane layer was collected. The aqueous layer was extracted with 600 mL of hexanes. The combined hexane layers were concentrated, and the residue purified on a silica gel column, eluting with 5-15% ethyl acetate in hexanes, to obtain spiro[bicyclo[2.2.1]heptane-2,1'-cyclopentan]-3-one (12.6 g, 33.8%) as oil. $^1$H NMR (CDCl$_3$, 400 MHz): δ 2.56 (d, J=5.1 Hz, 1 H), 2.24 (bs, 1 H), 1.44-1.88 (m, 14 H); LCMS (m/z): 165 (M+1).

To a suspension of (methyl)triphenylphosphonium bromide (17.6 g, 48.4 mmol) in THF (100 mL) at −78° C. was added n-butyllithium (18.1 mL of 2.5 M solution in THF, 45 mmol) and the mixture was stirred 30 min. To this mixture was added spiro[bicyclo[2.2.1]heptane-2,1'-cyclopentan]-3-one (5.30 g, 32.3 mmol), and the reaction was stirred at ambient temperature for 18 h. Hexanes (200 mL) were added, and the mixture was filtered. The filtrate was concentrated, and the residue was purified on an 80 g silica gel column, eluting with hexanes, to obtain 3-methylenespiro[bicyclo[2.2.1]heptane-2,1'-cyclopentane] (4.80 g, 91.7%) as oil.

Sulfuric acid (1.61 mL, 2.96 g, 30.2 mmol) was slowly added to a suspension of 3-methylenespiro[bicyclo[2.2.1]heptane-2,1'-cyclopentane]. (4.80 g, 29.6 mmol) and potassium thiocyanate. (2.96 g, 30.2 mmol) at 50° C. The reaction mixture was then stirred at 85° C. for 5.5 h, cooled to ambient temperature, diluted with toluene (30 mL) and washed with water (20 mL) followed by with saturated aqueous sodium bicarbonate (10 mL). The toluene layer was dried over anhydrous sodium sulfate and filtered To the filtrate was added sodium bis(methoxyethoxy)aluminum hydride (40% solution in toluene, 2 equivalents) and the reaction was stirred at 85° C. for 2 h. The reaction was cooled to 0° C., and a solution of 3N aqueous sodium hydroxide (20 mL) in 5% aqueous sodium hypochlorite (35 mL) was slowly added (drop-wise at intervals). The toluene layer was separated and washed with water (30 mL). The toluene layer was then extracted with 1N aqueous hydrochloric acid (2×10 mL) and discarded. The aqueous hydrochloric acid layer was made basic (to pH 10) by addition of 10% aqueous sodium hydroxide and extracted with diethyl ether. The diethyl ether extracts were concentrated, and the residue was purified by silica gel column chromatography, using 0-40% CMA (chloroform:methanol:30% aqueous ammonia, 9:1:0.1) in chloroform to obtain N,3-dimethylspiro[bicyclo[2.2.1]heptane-2,1'-cyclopentan]-3-amine (1.2 g, 53%) as oil. $^1$H NMR (CDCl$_3$, 400 MHz): δ 2.28 (s, 3H), 2.24 (bs, 1H), 1.84-1.76 (m, 2H), 1.73-1.68 (m, 1H), 1.62-1.52 (m, 4H), 1.48-1.24 (m, 7H), 1.09-1.05 (m, 1H), 1.04 (s, 3H); LCMS (m/z): 194 (M+1).

Example 4

General Procedure for Making N-substituted spiro[bicyclo[2.2.1]heptane-2,1'-cyclobutan]-3-amines Certain N-substituted spiro[bicyclo[2.2.1]heptane-2,1'-cyclobutan]-3-amines can be prepared by the reductive amination of spiro[bicyclo[2.2.1]heptane-2,1'-cyclobutan]-3-one. The following procedure, utilizing methylamine and providing N-methylspiro[bicyclo[2.2.1]heptane-2,1'-cyclobutan]-3-amine trifluoroacetate, is exemplary. Reductive aminations utilizing dimethylamine, azetidine, and pyrrolidine were performed in a similar fashion.

To a solution of spiro[bicyclo[2.2.1]heptane-2,1'-cyclobutan]-3-one (0.15 g, 1.0 mmol) and methylamine (4.0 mL of 2.0 M solution in THF, 8.0 mmol) in 1,2-dichloroethane (10 mL) was added acetic acid (0.2 mL) and sodium triacetoxyborohydride (0.85 g, 4.0 mmol). The reaction was stirred at ambient temperature for 48 h, diluted with dichloromethane (10 mL), washed with saturated aqueous sodium bicarbonate solution (10 mL), and concentrated. The residue was purified on preparative HPLC, eluting with mixtures of 0.05% formic acid in water and 0.05% formic acid in acetonitrile, Selected fractions were concentrated, and the residue was dissolved in methanol (2 mL). Trifluoroacetic acid (0.1 mL) was added, and the mixture was concentrated and vacuum dried to obtain N-methylspiro[bicyclo[2.2.1]heptane-2,1'-cyclobutan]-3-amine trifluoroacetate (0.088 g) as gum. $^1$H NMR (CD$_3$OD, 400 MHz): δ 3.06-3.02 (m, 1H), 2.568 (s, 3H), 2.54 (brs, 1H), 2.34 (brs, 1H), 2.02-1.83 (m, 6H). 1.56-1.42 (m, 5H), 1.26-1.32 (m, 1H); LCMS (m/z): 166 (M+1).

Example 5

(1S,3R,4R)—N,4,7,7-Tetramethylspiro[bicyclo[2.2.1]heptane-2,1'-cyclobutan]-3-amine hydrochloride and (1S,3S,4R)—N,4,7,7-tetramethylspiro[bicyclo[2.2.1]heptane-2,1'-cyclobutan]-3-amine hydrochloride The following chemistry, using D-camphor as a starting material, was repeated using L-camphor as a starling material, yielding products that are enantiomeric to those described here.

A mixture of D-(+)-camphor (4.40 g, 28.9 mmol) and sodium amide (2.50 g, 61.5 mmol) in toluene (100 mL) was stirred at 100° C. for 30 min. A solution of 1,3-dibromopropane (31.8 mmol, 3.24 mL, 6.42 g) in toluene (20 mL) was added, and the reaction was heated at reflux for 3 h. The reaction was cooled to ambient temperature, washed with water (100 mL), dried over anhydrous sodium sulfate and concentrated. The residue was dissolved in 5% methanol in dichloromethane (80 mL) and cooled to −78°C. Ozone was passed through the solution until the blue color persisted (~10 minutes). Dimethyl sulfide (2 mL) was then added, and the reaction was warmed slowly to ambient temperature. The reaction mixture was concentrated, and the residue was purified on a silica gel column (40 g), eluting with 0-20% ether in hexanes, to obtain (1S,4R)-4,7,7-trimethylspiro[bicyclo[2.2.1]heptane-2,1'-cyclobutan]-3-one (1.66 g, 29.9% yield) as oil. $^1$H NMR (CDCl$_3$, 400 MHz): δ 2.26 (m, 1H), 2.10-1.97 (m, 5H), 1.85-1.1.66 (m, 2H), 1.62-1.53 (m, 1H), 1.47-1.40 (m, 1H), 1.28-1.19 (m, 1H), 0.94 (s, 3H), 0.88 (s, 3H), 0.75 (s, 3H); LCMS (m/z): 193 (M+1).

A mixture of (1S,4R)-4,7,7-trimethylspiro[bicyclo[2.2.1]heptane-2,1'-cyclobutan]-3-one (1.60 g, 8.32 mmol) and formamide (10 mL) in formic acid (7 mL) was stirred at 175° C. for 72 h. The reaction mixture was cooled to ambient temperature, poured into 200 mL of ice-water, and extracted with ether (2×50 mL). The combined ether extracts were washed with water (40 mL), dried over anhydrous sodium sulfate and concentrated to obtain N-(4,7,7-trimethylspiro[bicyclo[2.2.1]heptane-2,1'-cyclobutan]-3-yl)formamide (1.55 g, 84.2% yield) as gum.

To a solution of N-(4,7,7-trimethylspiro[bicyclo[2.2.1]heptane-2,1'-cyclobutan]-3-yl)formamide (1.50 g, 6.78 mmol) in THF (40 mL) at 0° C. was slowly added lithium aluminum hydride (27.1 mmol, 27.1 mL of 1.0 M solution in THF). After complete addition, the reaction was refluxed for 48 h. The reaction mixture was cooled to 0° C. and quenched by addition, in portions, of solid sodium sulfate decahydrate (10 g). After stirring for 1 h, this mixture was filtered, and the filtrate was concentrated. The residue was purified on a 40 g silica gel column, using 0-100% CMA (chloroform:methanol:30% aqueous ammonia; 9:1:0.1) in chloroform as the eluent, to obtain an exo amine product, (1S,3R,4R)—N,4,7,7-tetramethylspiro[bicyclo[2.2.1]heptane-2.1'-cyclobutan]-3-amine (0.49 g; 35% yield), and an endo-amine product, (1S,3S,4R)—N,4,7,7-tetramethylspiro[bicyclo[2.2.1]heptane-2,1'-cyclobutan]-3-amine (0.30 g; 21% yield), both as oils. The two products were converted to their hydrochloride salts by dissolving each in 1 mL of concentrated hydrochloric acid and concentrating and vacuum drying the samples. $^1$H NMR of exo-(1S,3R,4R)—N,4,7,7-tetramethylspiro[bicyclo[2.2.1]heptane-2,1'-cyclobutan]-3-amine hydrochloride (D$_2$O 400 MHz): δ 2.80 (s, 3H), 2.72 (brs, 1H), 2.22-1.91 (m, 4H), 1.84-1.72 (m, 3H), 1.54-1.45 (m, 2H), 1.38-1.31 (m, 1H), 1.10-1.01 (m, 1H), 0.87 (s, 3H), 075 (s, 3H), 0.72 (s. 3H); LCMS (m/z): 208 (M+1). $^1$H NMR of endo-(1S,3S,4R)—N4, 7,7-tetramethylspiro[bicyclo[2.2.1]heptane-2,1'-cyclobutan]-3-amine hydrochloride ($D_2O$, 400 MHz); δ 3.12 (brs, 1H), 2.79 (s, 3H), 2.26-2.16 (m, 1H), 2.01-1.85 (m, 3H), 1.78-1.69 (m, 3H), 1.60-1.51 (m, 1H), 1.36-1.24 (m, 2H), 1.08-1.00 (m, 1H), 0.85 (s, 3H), 0.78 (s, 3H) 0.75 (s, 3H); LCMS (m/z): 208 (M+1).

Example 6

General Procedure for Converting Secondary Amines into N-methyl tertiary amines

Certain N-methyl tertiary amines can be prepared by the reductive amination of the corresponding secondary amines. The following procedure, utilizing formaldehyde and providing exo-(1S,3R,4R)—N,N,4,7,7-pentamethylspiro[bicyclo[2.2.1]heptane-2,1'-cyclobutan]-3-amine hydrochloride, is exemplary. Analogous N-methylation reactions were carried out on a variety of secondary amines.

To a solution of (1S,3R,4R)—N,4,7,7-tetramethylspiro[bicyclo[2.2.1]heptane-2,1'-cyclobutan]-3-amine (0.10 g, 0.48 mmol) and 30% aqueous formaldehyde (1 mL) in methanol (4 mL) was added sodium triacetoxyborohydride (0.31 g, 1.4 mmol), and the reaction was stirred at ambient temperature for 16 h. The reaction was quenched with saturated aqueous sodium bicarbonate solution (30 mL) and extracted with dichloromethane (2×30 mL). Formic acid (0.2 mL) was added to the combined organic extracts and they were concentrated on rotary evaporator. The residue was purified by preparative LCMS, using mixtures of 0.05% formic acid in water and 0.05% formic acid in acetonitrile. Selected fractions were combined, made basic (pH 9) by addition of 10% aqueous sodium hydroxide and extracted with dichloromethane (2×30 mL). The combined organic extracts were treated with 0.5 mL of concentrated hydrochloric acid, This mixture was concentrated and vacuum dried to obtain (1S,3R,4R)—N,N,4,7,7-pentamethylspiro[bicyclo[2.2.1]heptane-2,1'-cyclobutan]-3-amine hydrochloride (0.06 g) as white solid. $^1H$ NMR ($D_2O$, 400 MHz): δ 3.27 (s, 3H), 3.19 (s, 3H), 3.10 (s, 1H), 2.55-2.28 (m, 4H), 2.18-1.97 (m, 3H), 1.80-1.60 (m, 3H), 1.45-1.36 (m, 1H), 1.28 (s, 3H), 1.02 (s, 3H), 1.01 (s, 3H); LCMS (m/z); 222 (M+1).

Example 7

N-Methylspiro[bicyclo[2,2,1]heptane-2,1'-cyclopropan]-3-amine trifluoroacetate

Neat 3-methylene-2-norbornanone (8.9 g, 73 mmol), followed by neat diiodomethane (8.30 mL, 103 mmol), were added to a slurry of zinc-copper couple (9.1 g, 57 mmol) in diethyl ether (75 mL). The resulting mixture was heated at reflux for 6 h. A second portion of zinc-copper couple (10 g) was added, and reflux was continued for an additional 16 h. The reaction was then quenched with water (200 mL) and diluted with diethyl ether (200 mL). The biphasic mixture was filtered through a pad of diatomaceous earth. The organic layer was separated, washed with 10% aqueous hydrochloric acid (2×50 mL), dried over anhydrous magnesium sulfate and concentrated. The residue was passed through a silica gel column, eluting with dichloromethane. Selected fractions were concentrated, and the residue was vacuum distilled on a bulb-to-bulb distillation apparatus at 3 Torr, collecting spiro[bicyclo[2.2.1]heptane-2,1'-cyclopropan]-3-one (1.6 g) as oil, $^1H$ NMR ($CDCl_3$, 400 MHz): δ 2.71-2.69 (m, 1H), 2.06 (brs, 1H), 2.00-1.72 (m, 3H), 1.66-1.57 (m, 3H), 1.09-1.00 (m, 2H), 0.91-0.89 (m, 1H), 0.80-0.75 (m, 1H).

To a solution of spiro[bicyclo[2.2.1]heptane-2,1'-cyclopropan]-3-one (0.13 g, 0.96 mmol) and methylamine (4.0 mL of 2.0 M solution in THF, 8.0 mmol) in 1,2-dichloroethane (10 mL) was added acetic acid (0.2 mL) and sodium triacetoxyborohydride (0.85 g, 4.0 mmol) and the reaction was stirred at ambient temperature for 48 h. The reaction was diluted with dichloromethane (10 mL), washed with saturated aqueous sodium bicarbonate solution (10 mL), and concentrated. The residue was purified on preparative HPLC, eluting with mixtures of 0.05% formic acid in water and 0.05% formic acid in acetonitrile. Selected fractions were concentrated, and the residue was dissolved in methanol (2 mL). Trifluoroacetic acid (0.1 mL) was added, and the mixture was concentrated and vacuum dried, to obtain N-methylspiro[bicyclo[2.2.1]heptane-2,1'-cyclobutan]-3-amine trifluoroacetate (0.005 g) as gum. $^1H$ NMR ($CD_3OD$, 400 MHz): δ 2.76 (brs, 1H), 2.59 (s, 3H), 1.85-1.82 (m, 1H), 1.69-1.55 (m, 6H), 1.34-1.28 (m, 1H). 0.83-0.78 (m, 1H), 0.67-0.62 (m, 1H), 0.58-0.50 (m, 2H); LCMS (m/z): 152 (M+1).

Example 8

N,3-dimethylspiro[bicyclo[2.2.1]heptane-2,1'-cyclopropan]-3-amine hydrochloride

To a solution of (3-methylspiro[bicyclo[2.2.1]hept[5]ene-2,1'-cyclopropane]-3-yl)methanol (9.4 g, 57 mmol), prepared as described by Gream and Pincombe, Aust. J. Chem, 27: 543-565 (1974), herein incorporated by reference with regard to such preparation; in methanol (20 mL) was added 0.8 g 10% Pd/C (wet) under nitrogen. The atmosphere was replaced with hydrogen (50 psi), and the mixture was shaken for 4 h at ambient temperature. The reaction was then filtered through a pad of diatomaceous earth, which was then washed with methanol. The filtrate was concentrated to yield 9.60 g of (3-methylspiro[bicyclo[2.2.1]heptane-2,1'-cyclopropane]-3-yl)methanol as a white solid (99%).

To a stirred solution of chromium trioxide (8.0 g, 76 mmol) in water (30 mL) cooled in an ice bath, was added carefully 96% sulfuric acid (6.9 mL, 120 mmol). While continuing to cool and stir the oxidant solution in an ice bath, a solution of (3-methylspiro[bicyclo[2.2.1]heptane-2.1'-cyclopropane]-3-yl)methanol (9.5 g; 57 mmol) in acetone (115 mL) was added over a 20 min period. After complete addition, the reaction mixture was stirred for 3 h while warming to ambient temperature. The reaction was then diluted with water (45 mL) and ethyl acetate (200 mL). Slowly, sodium bisulfite powder was added until the brown color dissipated and the aqueous layer became blue. The phases were then separated, and the aqueous layer was washed with ethyl acetate (2×100 mL). The organic layers were combined and dried over anhydrous magnesium sulfate. The drying agent was removed by filtration, and the filtrate was concentrated to yield a green oil. The oil as purified by silica gel (200 g) column chromatography, using a 0-50% ethyl acetate in hexanes gradient. Selected fractions were combined and concentrated to yield 6.0 g of 3-methylspiro[bicyclo[2.2.1]heptane-2,1'-cyclopropane]-3-carboxylic acid as a white solid (58%).

To a stirred solution of 3-methylspiro[bicyclo[2.2.1]heptane-2,1'-cyclopropane]-3-carboxylic acid (2.8 g, 15 mmol) and triethylamine (2.6 mL, 18 mmol) in toluene (70 mL) cooled in an ice bath, was added diphenylphosphonic azide (3.5 mL, 16 mmol). The reaction mixture was warmed to 90° C. and stirred for 2.5 h. Benzyl alcohol (1.7 mL, 16 mmol) was then added to the reaction, and the mixture was stirred an additional 16 h at 90° C. The reaction mixture was cooled and concentrated. The residue was purified by silica gel (60 g)

column chromatography, using a 0-15% ethyl acetate in hexanes gradient. Selected fractions were combined and concentrated to yield 1.6 g of a mixture of materials, including, 3-isocyanato-3-methylspiro[bicyclo[2.2.1]heptane-2,1'-cyclopropane] and the corresponding benzyl carbamate, as a white solid. This mixture was dissolved in dry THF (16 mL) and cooled in an ice bath. Lithium aluminum hydride (8.5 mL of 2.0M in THF, 17 mmol) was slowly added. The reaction was warmed to 55° C. for 3 h. The reaction was then cooled in an ice-bath and diluted with diethyl ether (20 mL). The reaction was quenched by careful addition of water until gas evolution subsided. The resulting viscous white slurry was stirred at ambient temperature for 1 h, during which time the salts became more granular. The slurry was then filtered through a pad of diatomaceous earth, and the filter cake was washed with diethyl ether (10 mL) and then ethyl acetate (10 mL). The combined filtrates were extracted with 6M hydrochloric acid (3×4 mL). The aqueous extracts were combined and concentrated on a rotary evaporator to yield 1.6 g of N,3-dimethylspiro[bicyclo[2.2.1]heptane-2,1'-cyclopropan]-3-amine hydrochloride as a white solid (53% yield). $^1$H NMR (400 MHz, D$_2$O): δ 2.52 (s, 1H), 2.46 (a, 3H), 1.72 (d. J=11 Hz, 1H), 1.49-1.41 (m, 3H), 1.39-1.32 (m, 2H), 1.28 (d, J=11 Hz, 1H), 1.02 (s, 3H), 0.59-0.51 (m, 3H), 0.45-0.43 (m, 1H): LCMS (m/z): 166 (M+1).

Example 9

N,3-dimethylspiro[bicyclo[2.2.2]oct[5]ene-2,1'-cyclopenten]-3-amine hydrochloride and N,3-dimethylspiro[bicyclop[2.2.2]octane-2,1'-cyclopentan]-3-amine hydrochloride The intermediate, bicyclo[2,2,2]oct-5-en-2-one, was made using procedures described by Kozikowski and Schmiesing, J. Org. Chem. 48; 1000-1007 (1983), previously incorporated by reference with regard to such reaction; and then subsequently transformed into N,3-dimethylspiro[bicyclo[2.2.2]oct[5]ene-2,1'-cyclopentan]-3-amine and N,3-dimethylspiro[bicyclo[2.2.2]octane-2,1'-cyclopentan]-3-amine.

A mixture of acrylonitrile (79.4 g, 1.49 mol), 1,3-cyclohexadiene (60 g, 0.75 mol), and hydroquinone (1.1 g, 10 mmol) was sealed in a tube and heated at 120° C. for 18 h. The resulting mixture was concentrated and purified by chromatography on silica gel, eluting with mixtures of ethyl acetate (0.5% to 1%) in petroleum ether, to give a separable mixture of isomers (presumably endo/exo) of 5-cyanobicyclo[2,2,2] oct-2-ene (64 g, 64% yield) as a white semisolid, $^1$H NMR (300 MHz, CDCl$_3$) 1.32 (m, 2H), 1.75 (m, 3H), 2.04 (m, 1H), 2.43 (m, 1H), 2.62 (m, 1H), 2.78 (m, 1H), 6.23 (m, 1H). 6.30 (m, 1H); $^1$H NMR (300 MHz, CDCl$_3$) δ 1.28 (m, 2H), 1.50 (m, 3H), 1.94 (m, 1H), 2.68 (m, 2H), 2.87 (m, 1H), 6.29 (m, 1H), 6.44 (m, 1H); LCMS (m/z) 134 (M+1).

To a refluxing mixture of pyridine (14.2 g, 0.180 mol), phosphorus pentachloride (28.0 g, 0.135 mol), and chloroform (100 mL) was added drop-wise a solution of 5-cyanobicyclo[2,2,2]oct-2-ene (12 g, 90 mmol) in chloroform (50 mL). The resulting mixture was heated at reflux for 15 h, cooled, and poured onto ice. The organic layer was concentrated, and the residue was purified by chromatography on silica gel, eluting with mixtures of ethyl acetate (0.5% to 1%) in petroleum ether, to give 5-chloro-5-cyanobicyclo[2,2,2] oct-2-ene (14.3 g, 95% yield) as a white semisolid, $^1$H NMR (300 MHz, CDCl$_3$) δ 1.3-1.5 (m, 3H), 2.02-2.18 (m, 2H), 2.51 (m, 1H), 2.72 (m, 1H), 3.12 (m, 1H), 6.22 (m, 1H), 6.41 (m, 1H); GCMS (m/z); 167.

To a stirred solution of 5-chloro-5-cyanobicyclo[2,2,2]oct-2-ene (65 g, 0.39 mol) (representing several runs of the foregoing procedure) in dimethyl sulfoxide (500 mL) was added potassium hydroxide (87.4 g, 1.56 mol) and water (30 mL). The resulting mixture was stirred at room temperature for 15 h, diluted with water (1000 mL) and extracted with ether (4×500 mL). The combined ether extracts were washed with brine, dried over anhydrous sodium sulfate, and concentrated. The residue was purified by chromatography on silica gel, eluting with mixtures of diethyl ether (1% to 5%) in petroleum ether, to give bicyclo[2,2,2]oct-5-en-2-one (23.8 g. 50% yield) as a white solid, $^1$H NMR (300 MHz, CDCl$_3$) δ 1.53~1.84 (m, 4H), 2.01~2.02 (m, 2H), 2.96~2.99 (m, 1H), 3.11~3.13 (m, 1H), 6.15~6.21 (m, 1H), 6.43~6.48 (m, 1H); GCMS (m/z): 122.

n-Butyllithium (56.5 mL of 1.6 M in hexanes, 90.4 mmol) was added to a solution of diisopropylamine (11.2 mL, 8.05 g, 79.6 mmol) in dry THF (108 mL) at −78° C. The mixture was warmed to 0° C. and stirred for 30 min. The solution was again cooled to −78° C., and bicyclo[2,2,2]oct-5-en-2-one (5.00 g, 36.2 mmol) dissolved in THF (10 mL) was added. The reaction was stirred for 30 min at −78° C., and then hexamethylphosphoric triamide (13.9 mL, 14.3 g, 79.6 mmol) followed by 1,4-dibromobutane (4.76 mL, 8.59 g, 39.8 mmol) were added. The reaction mixture was warmed to ambient temperature, stirred for 16 h, quenched with saturated aqueous ammonium chloride (50 mL), diluted with ether (100 mL), and washed with water (3×50 mL). The organic layer was dried over anhydrous sodium sulfate, filtered, and concentrated. The residue was purified on a 120 g silica column, eluting with 100% hexanes for 4 column volumes, followed by a step gradient to 9:1 hexanes/ethyl acetate. Selected fractions were concentrated to yield spiro[bicyclo[2.2.2]oct[5]ene-2,1'-cyclopentan]-3-one (5.1 g; ~90% pure by GC/MS) as a clear oil. The material was carried forward without further purification, by dissolving in dry THF (20 mL) and cooling to −78° C. Methylmagnesium bromide (28.6 mL of 3.0 M in diethyl ether, 85.8 mmol) was then added, and the reaction was slowly warmed to ambient temperature. The reaction was stirred at ambient temperature for 18 h and quenched by careful addition of saturated aqueous ammonium chloride. The reaction was transferred to a separatory funnel, and the aqueous layer was removed. The organic layer was washed twice with water (10 mL), dried over anhydrous sodium sulfate, filtered, and concentrated. The remaining material (colorless oil) was a mixture of 3-methylspiro[bicyclo[2.2.2]oct[5]ene-2,1'-cyclopentan]-3-ol (4.9 g) and starting material.

Without further purification, the sample generated immediately above was combined with sodium cyanide (1.93 g, 37.8 mmol) in acetic acid (20 mL). This mixture was cooled to 0° C. and stirred at that temperature as sulfuric acid (20 mL) was slowly added. The reaction, which turned a deep red color upon complete addition of reagents, was stirred at ambient temperature for 18 h. It was then quenched with the addition of 100 mL water, made basic (pH 9) by addition of 3 M aqueous sodium hydroxide, and extracted with dichloromethane (4×50 mL). The combined organic layers were dried over anhydrous sodium sulfate and concentrated to obtain an off-white solid. The solid was dissolved in dry THF (200 mL), cooled to 0° C. and held at this temperature as a solution of lithium aluminum hydride (25.2 mL of 2 M in THF, 50.4 mmol) was slowly added. The reaction was heated to reflux for 18 h, cooled in ice-bath, and quenched by cautious addition of 5 g of sodium sulfate derahydrate. The resulting mixture was stirred for 30 min and filtered. The filtrate was concentrated, and the residue was purified on 120 g silica gel column, using 0-70% CMA in chloroform, providing N,3-dimethylspiro[bicyclo[2.2.2]oct[5]ene-2,1'-cyclopentan]-3-amine (0.20 g, 2.7% yield). This material was taken up in dichloromethane (5 ml), converted to the HCL salt by treating with 0.5 mL of 4 M hydrochloric acid in dioxane and concentrating the resulting mixture. The resultant amorphous solid was dissolved in methanol (3 mL) and precipitated with diethyl ether (3 mL). The solvent was removed by aspiration, and the precipitate was triturated three times with diethyl ether (3 mL). The sample of hydrochloride salt was then vacuum dried. $^1$H NMR (300 MHz, CD$_3$OD) δ 1.02 (s, 3H), 1.19-1.42 (m, 4H), 1.51-1.64 (m, 7H), 1.81 (m, 1H), 2.21 (m, 2H), 2.73 (s, 3H), 5.57 (dd, J=9 Hz, J$_2$=3 Hz, 1H), 6.01 (d, J=6 Hz, 1H), LCMS (m/z): 206 (M+1).

N,3-dimethylspiro[bicyclo[2.2.2]oct[5]ene-2,1'-cyclopentan]-3-amine (80 mg, 0.39 mmol) was dissolved in methanol (7.8 mL) and 10% Pd/C (wet) (41 mg) was added. This mixture was placed under a balloon of hydrogen gas and stirred at ambient temperature for 16 h. The reaction mixture was then filtered through diatomaceous earth, and the flit ate was concentrated, leaving N,3-dimethylspiro[bicyclo[2.2.2]octane-2,1'-cyclopentan]-3-amine (45 mg, 56% yield). This was dissolved in dichloromethane (3 mL), converted to its hydrochloric acid salt by treating with 0.3 mL of 4 M hydrochloric acid in dioxane, and concentrating the resulting mixture. The resultant amorphous solid was dissolved in methanol (3 mL) and precipitated with diethyl ether (1 mL). The solvent was removed by aspiration, and the precipitate was triturated three times with diethyl ether (3 mL). The sample of hydrochloride salt was then vacuum dried. $^1$H NMR (300 MHz, CD$_3$OD) δ 0.99 (s, 3H), 1.31 (m, 2H), 1.45-1.70 (m, 10H), 1.85 (m, 1H), 2.08 (m, 3H), 2.22-2.35 (m, 1H), 2.65 (s, 3H), 3.02 (m, 1H); LCMS (m/z): 20 (M+1).

VI. Biological Assays

Characterization of Interactions at Nicotinic Acetylcholine Receptors

Materials and Methods

Cell Lines. SH-EP1-human α4β2 (Eaton et al., 2003), SH-EP1-human α4β4 (Gentry at al., 2003) and SH-EP1-α6β3β4α5 (Grinevich et al., 2005) cell lines were obtained from Dr. Ron Lukas (Barrow Neurological Institute). The SH-EP1 cell lines, PC12, SH-SY5Y and TE671/RD cells were maintained in proliferative growth phase in Dulbecco's modified Eagle's medium (Invitrogen, Carlsbad, Calif.) with 10% horse serum (Invitrogen), 5% fetal bovine serum (Hy-Clone, Logan Utah), 1 nM sodium pyruvate, 4 mM L-glutamine. For maintenance of stable transfectants, the α4β2 and of α4β4 cell media was supplemented with 0.25 mg/mL zeocin and 0.13 mg/mL, hygromycin B. Selection was maintained for the of α6β3β4α5 cells with 0.25 mg/mL of zeocin, 0.13 mg/mL of hygromycin B, 0.4 mg/mL of geneticin, and 0.2 mg/mL of blasticidin.

Receptor Binding Assays

Preparation of Membranes from at Tissues. Rat cortices were obtained from Analytical Biological Services, Incorporated (ABS, Wilmington, Delaware). Tissues were dissected from female Sprague-Dawley rats, frozen and shipped on dry ice. Tissues were stored at 20° C. until needed for membrane preparation. Cortices from 10 rats were pooled and homogenized by Polytron (Kinematica GmbH, Switzerland) in 10 volumes (weight volume) of ice-cold preparative buffer (11 mM KCl, 6 mM KH$_2$PO$_4$, 137 mM NaCl, 8 mM Na$_2$HPO$_4$, 20 mM HEPES (free acid), 5 mM iodoacetamide, 1.5 mM EDTA, 0.1 mM PMSF pH 7.4). The resulting homogenate was centrifuged at 40,000 g for 20 minutes at 4° C. and the resulting pellet was re-suspended in 20 volumes of ice-cold water. After 60 minute incubation at 4° C., a new pellet was collected by centrifugation at 40,000 g for 20 minutes at 4° C. The final pellet was re-suspended in preparative buffer and stored at –20° C. On the day of the assay, tissue was thawed, centrifuged at 40,000 g for 20 minutes and then re-suspended in Dulbecco's Phosphate Buffered Saline, pH 7.4 (PBS, Invitrogen) to a final concentration of 2-3 mg protein/mL. Protein concentrations were determined using the Pierce BCA Protein Assay kit (Pierce Biotechnology, Rockford, Ill.), with bovine serum albumin as the standard.

Preparation of Membranes from Clonal Cell Lines. Cells were harvested in ice-cold PBS, pH 7.4, then homogenized with a Polytron (Kinematica GmbH, Switzerland). Homogenates were centrifuged at 40,000 g for 20 minutes (4° C.). The pellet was re-suspended in PBS and protein concentration determined using the Pierce BCA Protein Assay kit (Pierce Biotechnology, Rockford, Ill.).

Competition Binding to Receptors in Membrane Preparations. Binding to nicotinic receptors was assayed on membranes using standard methods adapted from published procedures (Lippiello and Fernandes 1986 Davies et al., 1999). In brief, membranes were reconstituted from frozen stocks and incubated for 2 h on ice in 150 µl assay buffer (PBS) in the presence of competitor compound (0.001 nM to 100 µM) and radioligand. [$^3$H]-nicotine (L-(–)-[N-methyl-$^3$H]-nicotine, 69.5 Ci/mmol, Perkin-Elmer Life Sciences, Waltham, Mass.) was used for human α4β2 binding studies. [$^3$H]-epibatidine (52 Ci/mmol, Perkin-Elmer Life Sciences) was used for binding studies at the other nicotinic receptor subtypes. L-[Benzilic-4,4-$^3$H] Quinuclidynyl Benzilate ([$^3$H]QNB) was used for muscarinic receptor binding studies. Incubation was terminated by rapid filtration on a multimanifold tissue harvester (Brandel, Gaithersburg, Md.) using GF/B filters pre-soaked in 0.33% polyethyleneimine (w/v) to reduce nonspecific binding. Alters were washed 3 times with ice-cold PBS and the retained radioactivity was determined by liquid scintillation counting.

Binding Data Analysis. Binding data were expressed as percent total control binding. Replicates for each point were averaged and plotted against the log of drug concentration. The IC$_{50}$ (concentration of the compound that produces 50% inhibition of binding) was determined by least squares non-linear regression using GraphPad Prism software (GraphPAD, San Diego, Calif.). Ki was calculated using the Cheng-Prusoff equation (Cheng and Prusoff, 1973).

Calcium Flux Functional Assays

Twenty-four to forty-eight hours prior to each experiment, cells were plated in 96 well black-walled, clear bottom plates (Corning, Corning, N.Y.) at 60-100,000 cells/well. On the day of the experiment, growth medium was gently removed, 200 µL 1×FLIPR Calcium 4 Assay reagent (Molecular Devices, Sunnyvale, Calif.) in assay buffer (20 mM HEPES, 7 mM TRIS base, 4 mM CaCl$_2$, 5 mM D-glucose, 0.8 mM MgSO$_4$, 5 mM KCl, 0.8 mM MgCl$_2$, 120 nM N-methyl D-glucamine, 20 mM NaCl, pH 7.4 for SH-EP1-human α4β2 cells or 10 mM HEPES, 2.5 mM CaCl$_2$, 5.6 mM D-glucose, 0.8 mM MgSO$_4$, 5.3 mM KCl, 138 mM NaCl, pH 7.4 with TRIS-base for all other cell lines) was added to each well and plates were incubated at 37° C. for 1 hour (29° C. for the 29° C.-treated SH-EP1-human α4β2 cells). For inhibition studies, competitor compound (10 pM-10 µM) was added at the time of dye addition. The plates were removed from the incubator and allowed to equilibrate to room temperature. Plates were transferred to a FLIPR Tetra fluorometric imaging plate reader (Molecular Devices) for addition of compound and monitoring of fluorescence (excitation 485 nm, emission 525 nm). The amount of calcium flux was compared to both a positive (nicotine) and negative control (buffer alone). The positive control was defined as 100% response and the results of the test compounds were expressed as a percentage of the positive control For inhibition studies, the agonist nicotine was used at concentrations of 1 µM for SH-EP1-human α4β2 and SH-EP1-human α4β4 cells, 10 µM for PC12 and SH-SY5Y cells, and 100 µM for TE671/RD cells.

Neurotransmitter Release

Dopamine release studies were performed using striatal synaptosomes obtained from rat brain as previously described (Bencherif et al., 1998). Striate tissue from two rats (female, Sprague-Dawley, weighing 150-250 g) was pooled and homogenized in ice-cold 0.32 M sucrose (8 mL) containing 5 mM HEPES, pH 7.4, using a glass/glass homogenizer. The tissue was then centrifuged at 1.000×g for 10 minutes. The pellet was discarded and the supernatant was centrifuged at 12,500×g for 20 minutes. The resulting pellet was re-suspended in ice-cold perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 minutes at 23,000×g. The final pellet was re-suspended in perfusion buffer (2 mL) for immediate use.

The synaptosomal suspension was incubated for 10 minutes in a 37° C. shaking incubator to restore metabolic activity. [$^3$H]Dopamine ([$^3$H]DA, specific activity=28.0 Ci/mmol, NEN Research Products) was added at a final concentration of 0.1 µM and the suspension was incubated at 37° C. for another 10 minutes. Aliquots of perfusion buffer (100 µL) and tissue (100 µL) were loaded into the suprafusion chambers of a Brandel Suprafusion System (series 2500, Gaithersburg, Md.). Perfusion buffer (room temperature) was pumped into the chambers at a rate of approximately 0.6 mL/min for a wash period of 8 min. Competitor compound (10 pM-100 nM) was applied in the perfusion stream for 8 minutes. Nicotine (10 µM) was then applied in the perfusion stream for 48 seconds. Fractions (12 seconds each) were continuously collected from each chamber throughout the experiment to capture basal release and agonist-induced peak release and to re-establish the baseline after the agonist application. The perfusate was collected directly into scintillation vials, to which scintillation fluid was added. Released [$^3$H]DA was quantified by scintillation counting. For each chamber, the integrated area of the peak was normalized to its baseline.

Release was expressed as a percentage of release obtained with control nicotine in the absence of competitor. Within each assay, each test compound concentration was replicated using 2 chambers; replicates were averaged. The compound concentration resulting in half maximal inhibition ($IC_{50}$) of specific ion flux was defined.

Patch Clamp Electrophysiology

Cell Handling. After removal of GH4C1-rat T6'S α7 cells from the incubator, medium was aspirated, cells trypsinized for 3 minutes, gently triturated to detach them from the plate, washed twice with recording medium, and re-suspended in 2 ml of external solution (see below for composition). Cells were placed in the Dynaflow chip mount on the stage of an inverted Zeiss microscope (Carl Zeiss Inc., Thornwood, N.Y.). On average, 5 minutes was necessary before the whole-cell recording configuration was established. To avoid modification of the cell conditions, a single cell was recorded per single load. To evoke short responses, compounds were applied for 0.5 s using a Dynaflow system (Cellectricon, Inc., Gaithersburg, Md.), where each channel delivered pressure driven solutions at either 50 or 150 psi.

Electrophysiology.

Conventional whole-cell current recordings were used. Glass microelectrodes (5-10 MΩ resistance) were used to form tight seals (>1 GΩ) on the cell surface until suction was applied to convert to conventional whole-cell recording, The cells were then voltage-clamped at holding potentials of −60 mV, and ion currents in response to application of ligands were measured. Whole-cell currents recorded with an Axon 700A amplifier were filtered at 1 kHz and sampled at 5 kHz by an ADC board 1440 (Molecular Devices). Whole-cell access resistance was less than 20 MΩ. Data acquisition of whole-cell currents was done using a Clampex 10 (Molecular Devices, Sunnyvale, Calif.), and the results were plotted using Prism 5.0 (GraphPad Software Inc., San Diego, Calif.). The experimental data are presented as the mean±S.E.M., and comparisons of different conditions were analyzed for statistical significance using Student's t and Two Way ANOVA tests. All experiments were performed at room temperature (22±1° C.). Concentration-response profiles were fit to the Hill equation and analyzed using Prism 5.0.

Solutions and Drug Application. The standard external solution contained: 120 mM NaCl, 3 mM KCl, 2 mM $MgCl_2$, 2 mM $CaCl_2$, 25 mM D-glucose, and 10 mM HEPES and was adjusted to pH 7.4 with Tris base. Internal solution for whole-cell recordings consisted of: 110 mM Iris phosphate dibasic, 28 mM Tris base, 11 mM EGTA, 2 mM $MgCl_2$, 0.1 mM $CaCl_2$ and 4 mM Mg-ATP, pH 7.3. (Liu et al., 2008). To initiate whole-cell current responses, compounds were delivered by moving cells from the control solution to agonist-containing solution and back so that solution exchange occurred within ~50 ms (based on 10-90% peak current rise times). Intervals between compound applications (0.5-1 min) were adjusted specifically to ensure the stability of receptor responsiveness (without functional rundown), and the selection of pipette solutions used in most of the studies described here was made with the same objective. (−)-Nicotine and acetylcholine (ACh), were purchased from Sigma-Aldrich (St. Louis, Mo.). All drugs were prepared daily from stock solutions.

To determine the inhibition of ACh induced currents by compounds of the present invention, we established a stable baseline recording applying 70 µM ACh (usually stable 5-10 consecutive applications). Then ACh (70 µM) was co-applied with test compound in a concentration range of 1 nM to 10 µM. Since tail of the current (current measured at the end of 0.5 s ACh application) underwent the most profound changes, inhibition and recovery plots represent amplitude of tail current.

Tabulated Summary

As shown in Table 1, compounds representative of the present invention typically exhibit inhibition constants (Ki values) for human α4β2 and ganglionic receptor subtypes in the 1-100 mM range, indicating a low affinity for the orthosteric binding sites (i.e. the binding site of the competitive agonist) of these receptor subtypes. The data in Table 1, however, also illustrates that compounds representative of the present invention effectively inhibit ion flux for these receptor subtypes, with typical $IC_{50}$ values of less than about 2 mM and typical $I_{max}$ values of >95%. Taken together, this data demonstrates that the compounds representative of this invention are effective at inhibiting ion flux mediated by these receptor subtypes through a mechanism that does not involve binding at the orthosteric sites.

TABLE 4

| Structure | Human α4β2 Ki (nM) | Human Ganglion Ki (nM) | Human α4β2 Ca Flux IC50 [29C/HS] (nM) | Human α4β2 Ca Flux Imax [29C/HS] (% inh) | Human α4β2 Ca Flux IC50 [37C/LS] (nM) | Human α4β2 Ca Flux Imax [37C/LS] (% inh) | Human Ganglion Ca Flux IC50 (nM) | Human Ganglion Ca Flux Imax (% inh) |
|---|---|---|---|---|---|---|---|---|
| | >10,000 | >10,000 | 1000 | 99 | 500 | 97 | 160 | 97 |
| 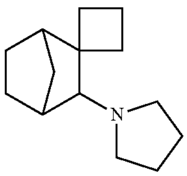 [SMILES: C1CCN(C2C3CCC(C3)C23CCC3)C1] | 3800 | >10,000 | 1400 | 99 | 59 | 96 | 190 | 79 |
| 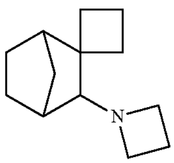 [SMILES: C1CN(C2C3CCC(C3)C23CCC3)C1] | 10,000 | >10,000 | 1400 | 96 | 740 | 98 | 190 | 89 |
| 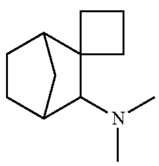 | 2600 | >10,000 | 1800 | 98 | 620 | 98 | 230 | 98 |
| 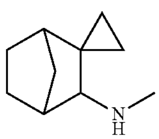 | 540 | >10,000 | 2100 | 97 | 570 | 93 | 440 | 93 |
| racemic | 8700 | >10,000 | 610 | 98 | 230 | 95 | 98 | 93 |
| peak 1 | >10,000 | >10,000 | 210 | 98 | 97 | 96 | 23 | 100 |
| peak 2 | >10,000 | >10,000 | 260 | 98 | 65 | 94 | 40 | 98 |
| | >10,000 | >10,000 | 1300 | 99 | 490 | 96 | 180 | 97 |

TABLE 4-continued

| Structure | Human α4β2 Ki (nM) | Human Ganglion Ki (nM) | Human α4β2 Ca Flux IC50 [29C/HS] (nM) | Human α4β2 Ca Flux Imax [29C/HS] (% inh) | Human α4β2 Ca Flux IC50 [37C/LS] (nM) | Human α4β2 Ca Flux Imax [37C/LS] (% inh) | Human Ganglion Ca Flux IC50 (nM) | Human Ganglion Ca Flux Imax (% inh) |
|---|---|---|---|---|---|---|---|---|
| 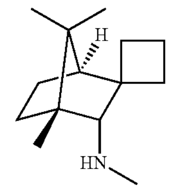 [SMILES: CN(C)C1C2(CCC2)[C@H]2CC[C@]1(C)C2(C)C] | 5600 | >10,000 | 710 | 98 | 430 | 96 | 74 | 99 |
| | >10,000 | >10,000 | 1000 | 97 | 600 | 96 | 98 | 95 |
| | >10,000 | >10,000 | 310 | 97 | 270 | 93 | 60 | 97 |
| | >10,000 | >10,000 | 540 | 96 | 520 | 97 | 100 | 98 |
| | >10,000 | >10,000 | 140 | 96 | 350 | 95 | 66 | 97 |
| 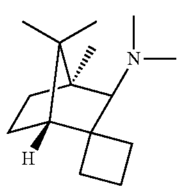 [SMILES: CN(C)C1C2(CCC2)[C@@H]2CC[C@@]1(C)C2(C)C] | 3200 | >10,000 | 1100 | 96 | 280 | 95 | 65 | 95 |
| 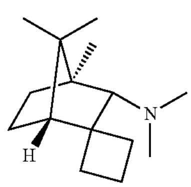 [SMILES: CN(C)C1C2(CCC2)[C@@H]2CC[C@@]1(C)C2(C)C] | 2600 | >10,000 | 740 | 95 | 380 | 95 | 86 | 99 |
| | >10,000 | >10,000 | 1100 | 99 | 120 | 100 | 35 | 96 |

TABLE 4-continued

| Structure | Human α4β2 Ki (nM) | Human Ganglion Ki (nM) | Human α4β2 Ca Flux IC50 [29C/HS] (nM) | Human α4β2 Ca Flux Imax [29C/HS] (% inh) | Human α4β2 Ca Flux IC50 [37C/LS] (nM) | Human α4β2 Ca Flux Imax [37C/LS] (% inh) | Human Ganglion Ca Flux IC50 (nM) | Human Ganglion Ca Flux Imax (% inh) |
|---|---|---|---|---|---|---|---|---|
| 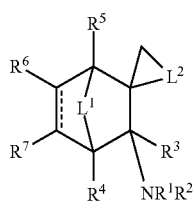 | >10,000 | >10,000 | 380 | 97 | 120 | 93 | 170 | 98 |
| 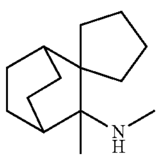 | 300 | >10,000 | | | 400 | 95 | 240 | 92 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of Formula I:

Formula I wherein
each of $R^1$ and $R^2$ individually is H, $C_{1-6}$ alkyl, or aryl-substituted $C_{1-6}$ alkyl, or $R^1$ and $R^2$ combine with the nitrogen atom to which they are attached to form a 3- to 8-membered ring, which ring may be optionally substituted with $C_{1-6}$ alkyl, aryl, $C_{1-6}$ alkoxy, or aryloxy substituents;
$R^3$ is H, $C_{1-6}$ alkyl, or $C_{1-6}$ alkoxy-substituted $C_{1-6}$ alkyl;
each of $R^4$, $R^5$, $R^6$, and $R^7$ individually is H, $C_{1-6}$ alkyl, or $C_{1-6}$ alkoxy;
$L^1$ is a linker species selected from the group consisting of $CR^8R^9$, $CR^8R^9CR^{10}R^{11}$, and O;
$L^2$ is a linker species selected from the group consisting of $CH_2$, $CH_2CH_2$, $CH_2CH_2CH_2$, and $CH_2CH_2CH_2CH_2$;
each of $R^8$, $R^9$, $R^{10}$, and $R^{11}$ individually is hydrogen or $C_{1-6}$ alkyl; and
the dashed line indicates an optional double bond;
or a pharmaceutically acceptable salt thereof.

2. The compound of claim 1, wherein $R^1$ is H and $R^2$ is $C_{1-6}$ alkyl.

3. The compound of claim 1, wherein $R^3$ is $C_{1-6}$ alkyl.

4. The compound of claim 1, wherein each of $R^4$, $R^5$, $R^6$, and $R^7$ is H.

5. The compound of claim 1, wherein $L^1$ is $CR^8R^9$, and each of $R^8$ and $R^9$ is hydrogen.

6. The compound of claim 1, wherein $L^2$ is $CH_2CH_2$.

7. The compound of claim 1, wherein the dashed line is a single bond.

8. A pharmaceutical composition comprising a compound as claimed in claim 1 and a pharmaceutically acceptable carrier.

9. A compound

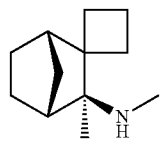

or a pharmaceutically acceptable salt thereof.

10. A pharmaceutical composition comprising a compound as claimed in claim 9 and a pharmaceutically acceptable carrier.

* * * * *